United States Patent
Makarov et al.

(10) Patent No.: US 10,544,472 B2
(45) Date of Patent: Jan. 28, 2020

(54) MULTIPLEXING TRANSCRIPTION FACTOR REPORTER PROTEIN ASSAY PROCESS AND SYSTEM

(71) Applicant: Attagene, Inc., Research Triangle Park, NC (US)

(72) Inventors: Sergei S. Makarov, Morrisville, NC (US); Ming Zheng, Chapel Hill, NC (US)

(73) Assignee: ATTAGENE, INC., Research Triangle Park, NC (US)

( * ) Notice: Subject to any disclaimer, the term of this patent is extended or adjusted under 35 U.S.C. 154(b) by 0 days.

(21) Appl. No.: 15/112,250

(22) PCT Filed: Jan. 9, 2015

(86) PCT No.: PCT/US2015/010724
§ 371 (c)(1),
(2) Date: Jul. 18, 2016

(87) PCT Pub. No.: WO2015/108763
PCT Pub. Date: Jul. 23, 2015

(65) Prior Publication Data
US 2016/0333428 A1 Nov. 17, 2016

Related U.S. Application Data

(60) Provisional application No. 61/929,043, filed on Jan. 18, 2014.

(51) Int. Cl.
C12Q 1/6897 (2018.01)
C12Q 1/6886 (2018.01)
G01N 33/50 (2006.01)

(52) U.S. Cl.
CPC ......... *C12Q 1/6897* (2013.01); *C12Q 1/6886* (2013.01); *G01N 33/5014* (2013.01); *G01N 2500/10* (2013.01)

(58) Field of Classification Search
CPC .................................................. C12Q 1/6897
See application file for complete search history.

(56) References Cited

U.S. PATENT DOCUMENTS

2004/0214236 A1* 10/2004 Brines ................ G01N 33/5088
435/7.2
2006/0160108 A1* 7/2006 Romanov ............ C12Q 1/6897
435/6.13
2009/0018031 A1* 1/2009 Trinklein ........... C12N 15/1051
506/10

FOREIGN PATENT DOCUMENTS

WO 2005045426 A2 5/2005
WO 2006062684 A2 6/2006
WO 2007038757 A2 4/2007
WO WO-2013154429 A1 * 10/2013 ............... C12Q 1/66

OTHER PUBLICATIONS

Van Rijn et al. Abstract 321. Transcription factor activity analysis using a functional multiplex Gaussia luciferase-based reporter assay. Molecular Therapy, vol. 21, Supplement 1, May 2013, pp. S123-S124, presented May 17, 2013, Salt Lake City, UT.*
Brizzard et al. Epitope tagging. BioTechniques, vol. 44, No. 5, pp. 693-695, May 2008.*
Van Rijn et al. Functional multiplex reporter assay using tagged Gaussi luciferase. Scientific Reports, vol. 3, p. 1046, Jan. 10, 2013, printed as pp. 1/6-6/6, including Supplementary Information, printed as pp. 1/3-3/3.*
Lewandrowski et al. (2014) In: Badr C. (eds) Bioluminescent Imaging. Methods in Molecular Biology (Methods and Protocols) vol. 1098. Humana Press, Totowa, NJ, first online Oct. 4, 2013. (Year: 2013).*
Romanov, S., et al., "Homogeneous reporter system enables quantitative functional assessment of multiple transcription factors", "Nature Methods", Feb. 24, 2008, pp. 253-260, vol. 5, No. 3.

* cited by examiner

*Primary Examiner* — Jennifer Dunston
(74) *Attorney, Agent, or Firm* — Hultquist, PLLC; Steven J. Hultquist

(57) ABSTRACT

A protein reporter system comprising at least one reporter including a response element responsive to the binding of a transcription factor, a secreted enzyme backbone and a recognition region for specific binding of an antibody. Multiplexed assays for binding, assaying and quantifying the activity of transcription factors are also described, in which the assays use protein reporters in sets, libraries or other groupings, as necessary to achieve desired quantification.

7 Claims, 34 Drawing Sheets

Specification includes a Sequence Listing.

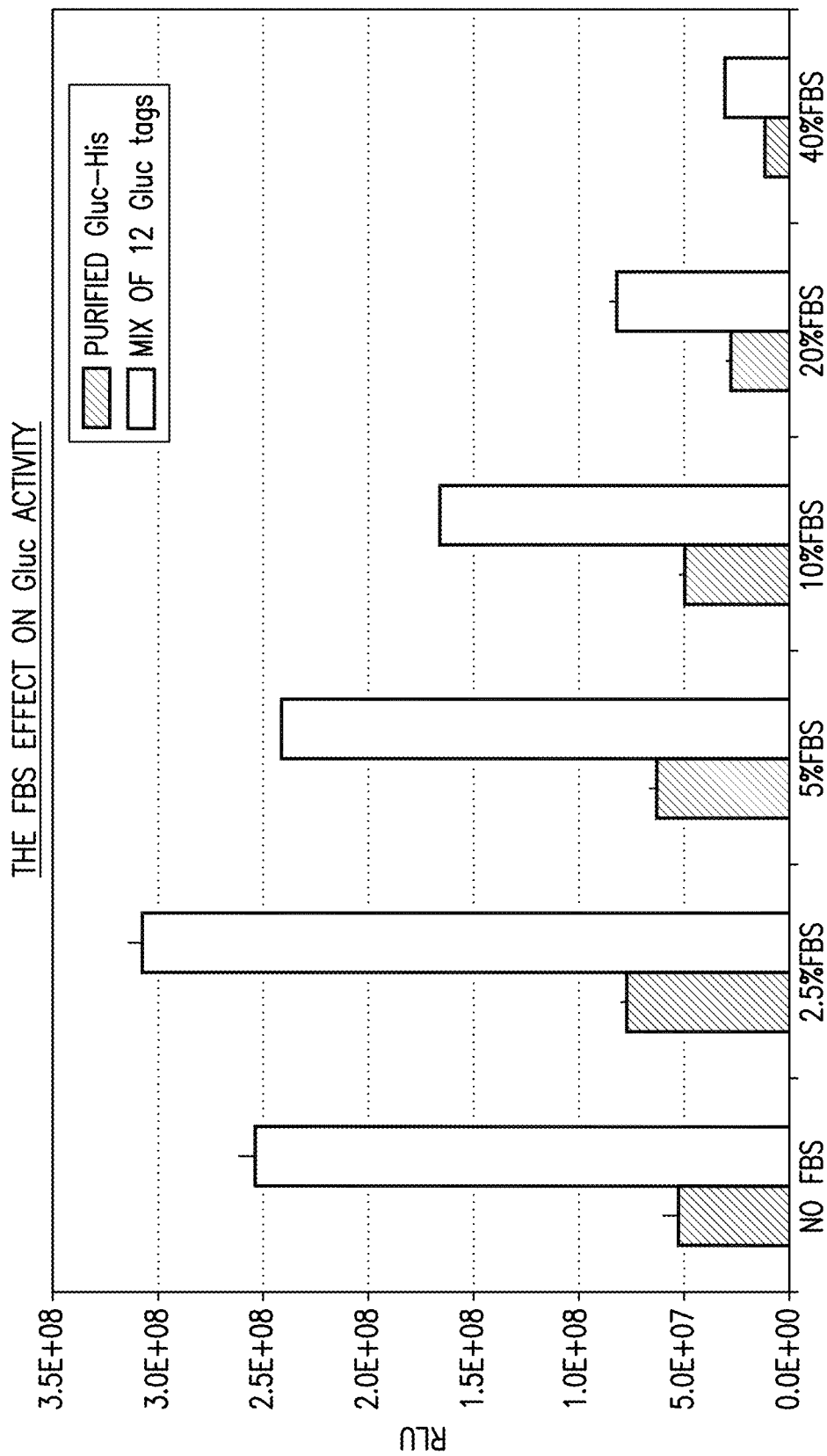

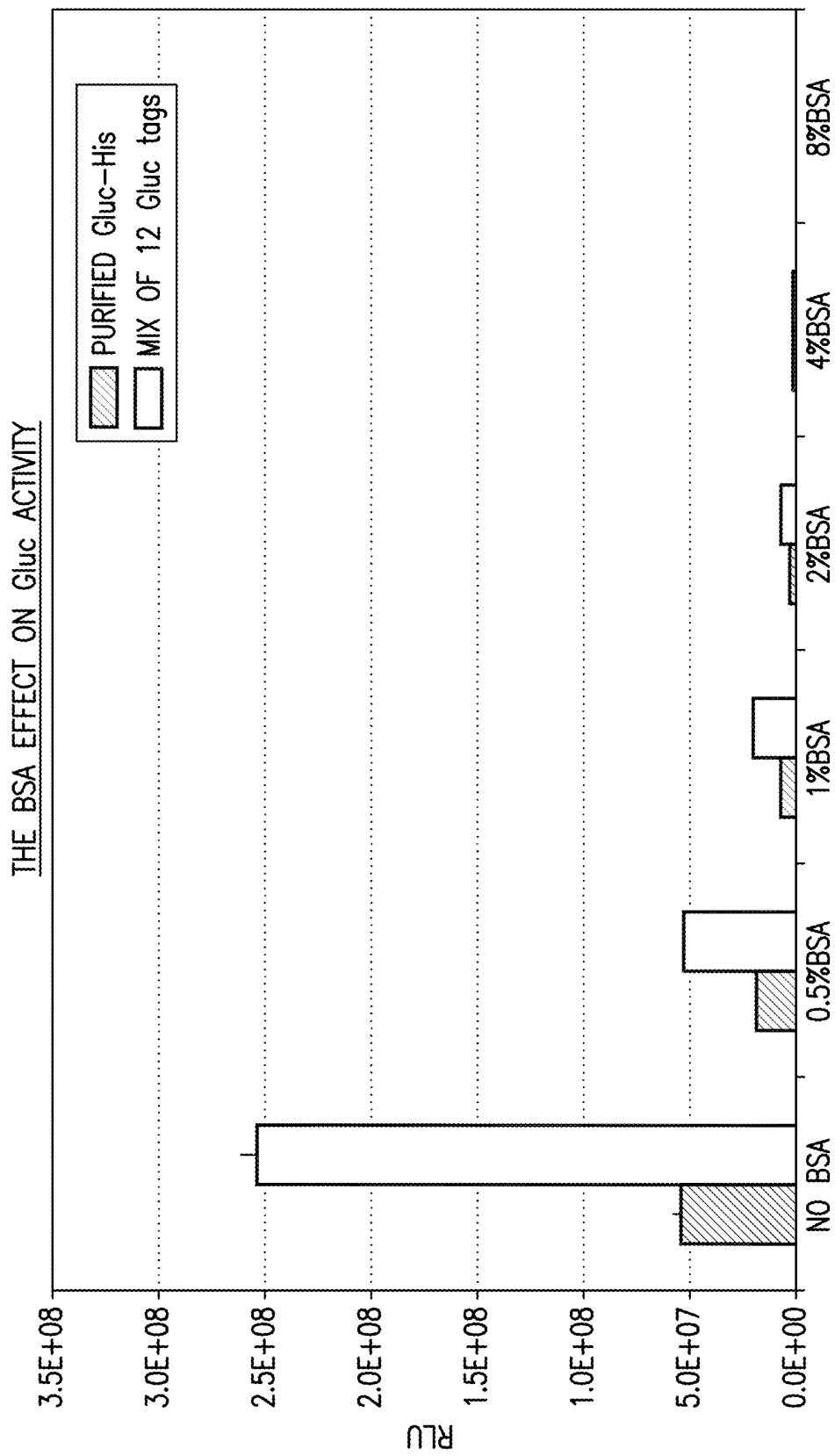

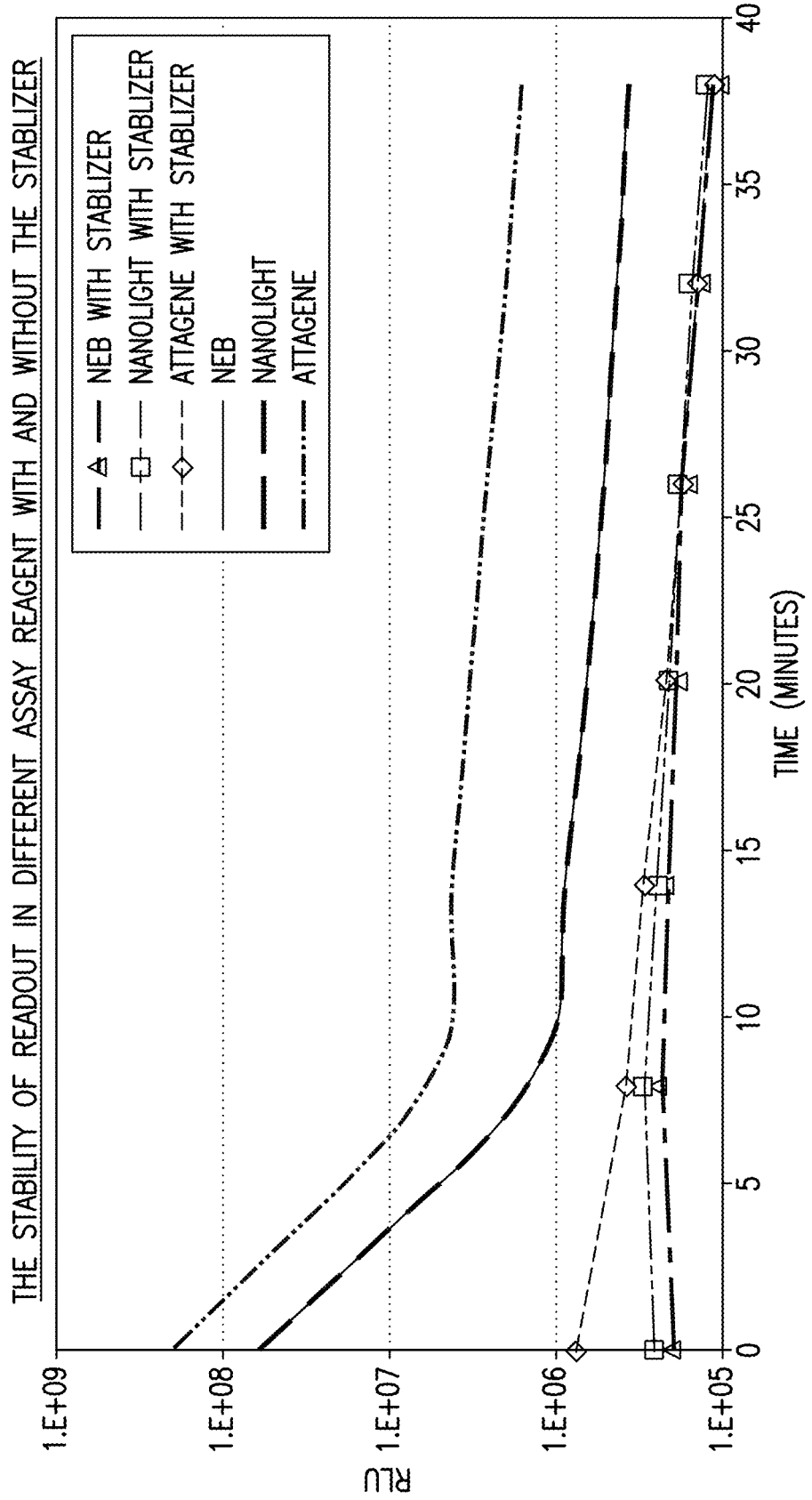

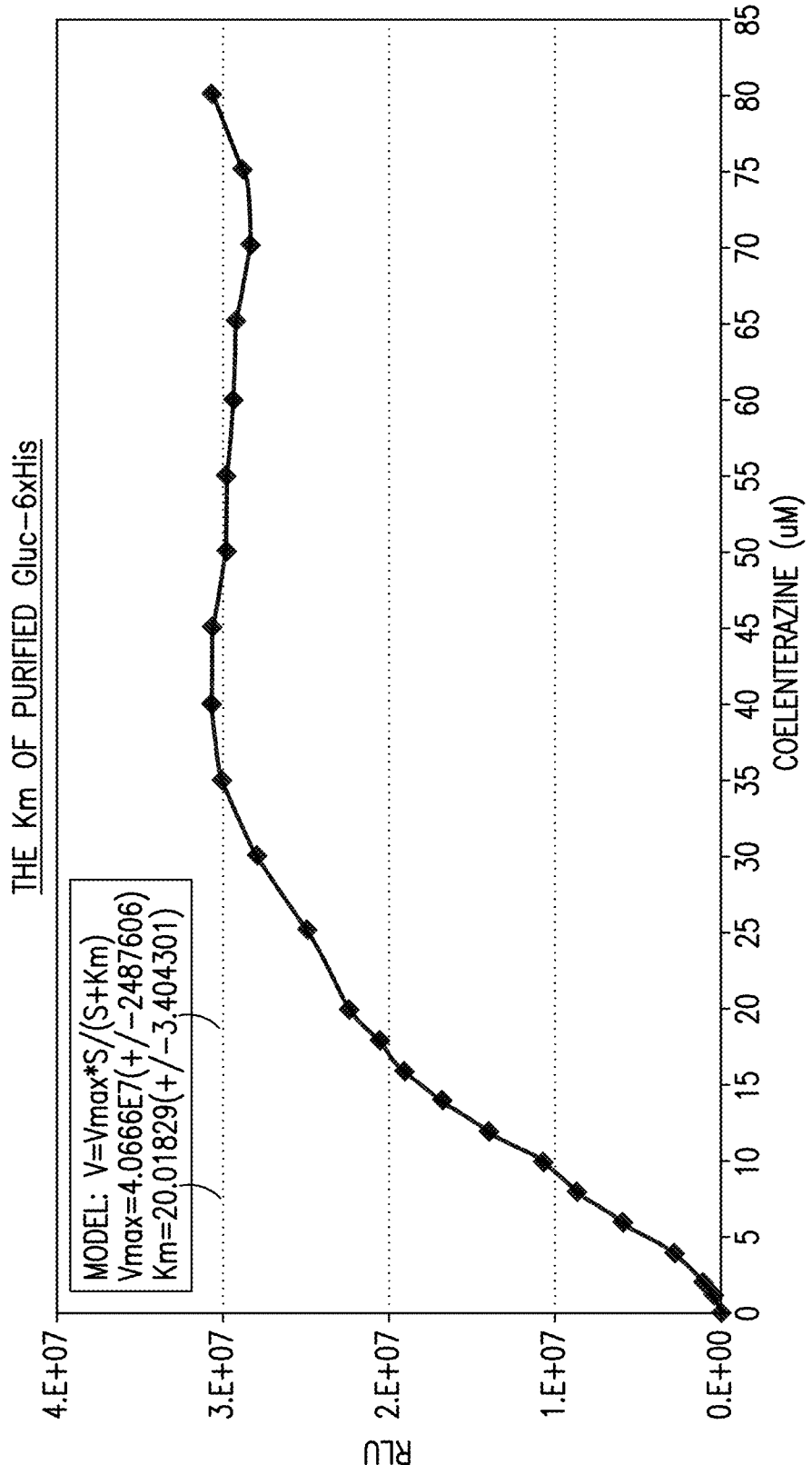

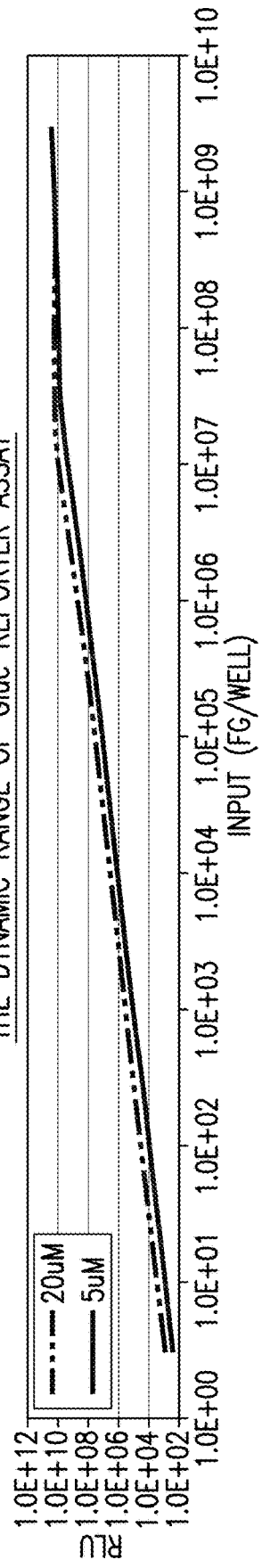
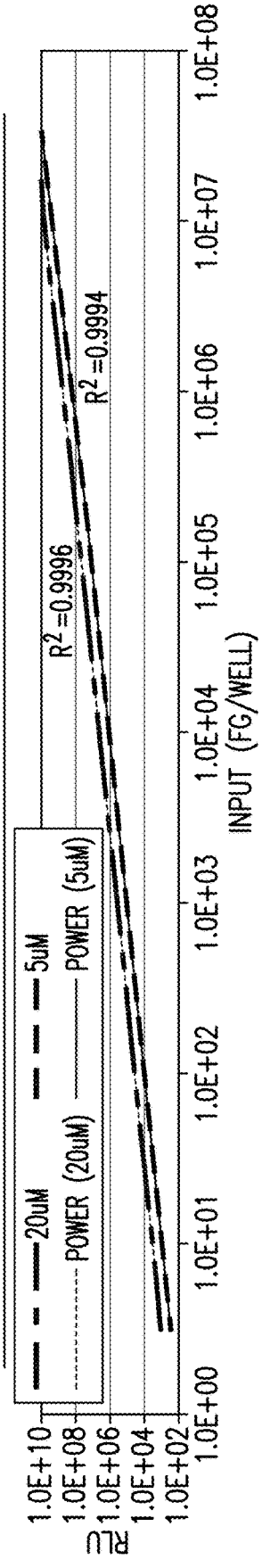

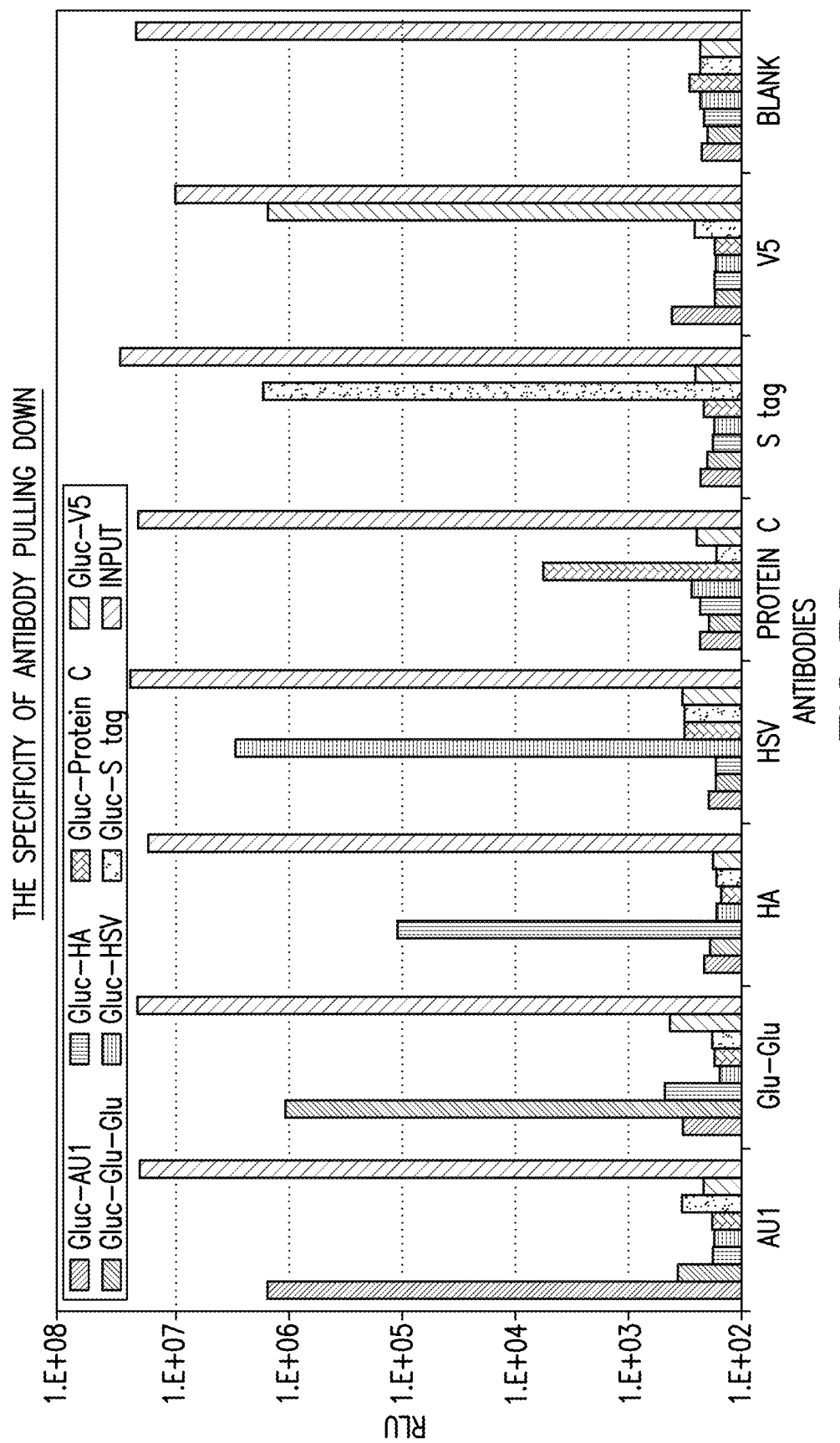

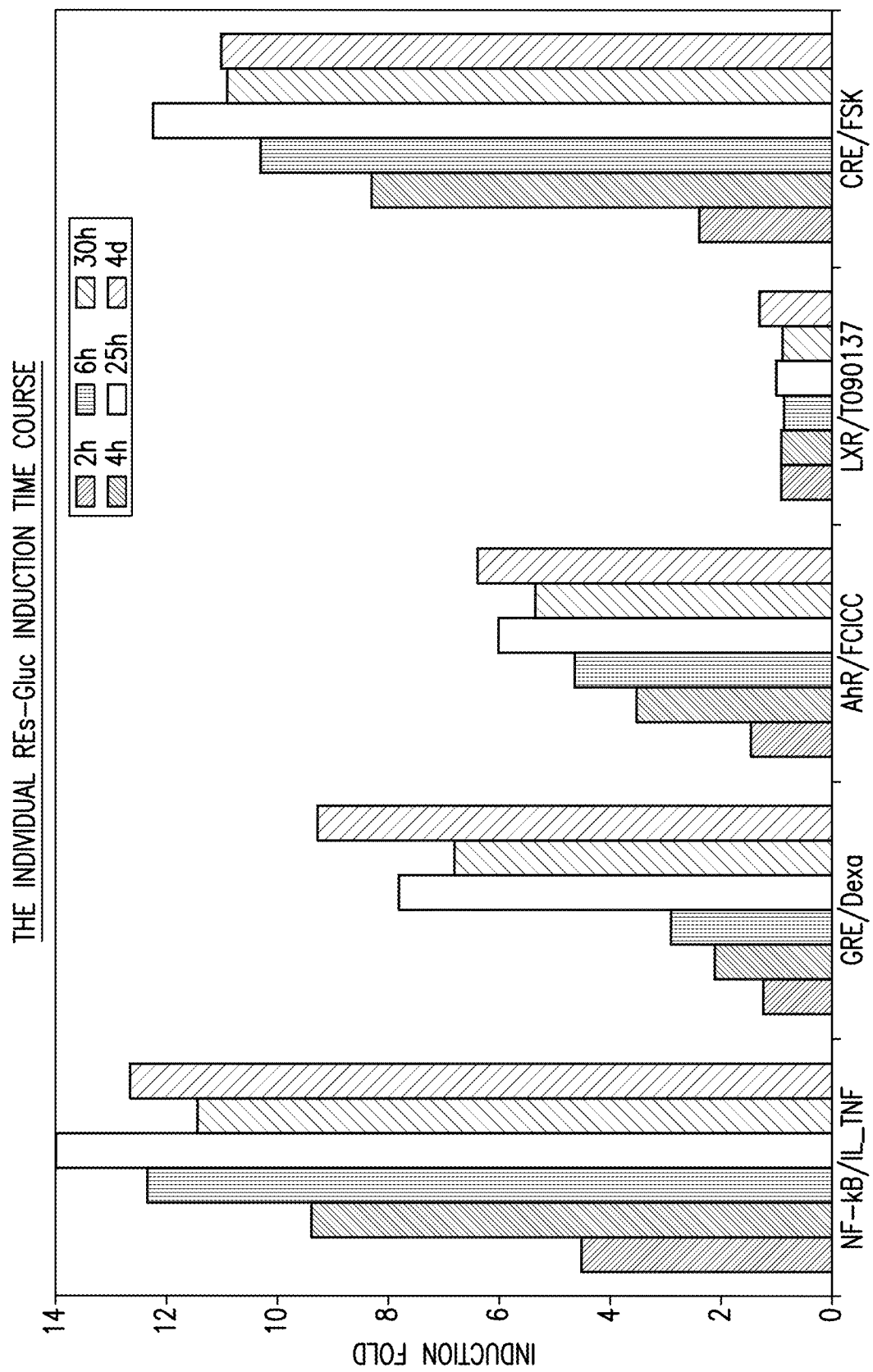

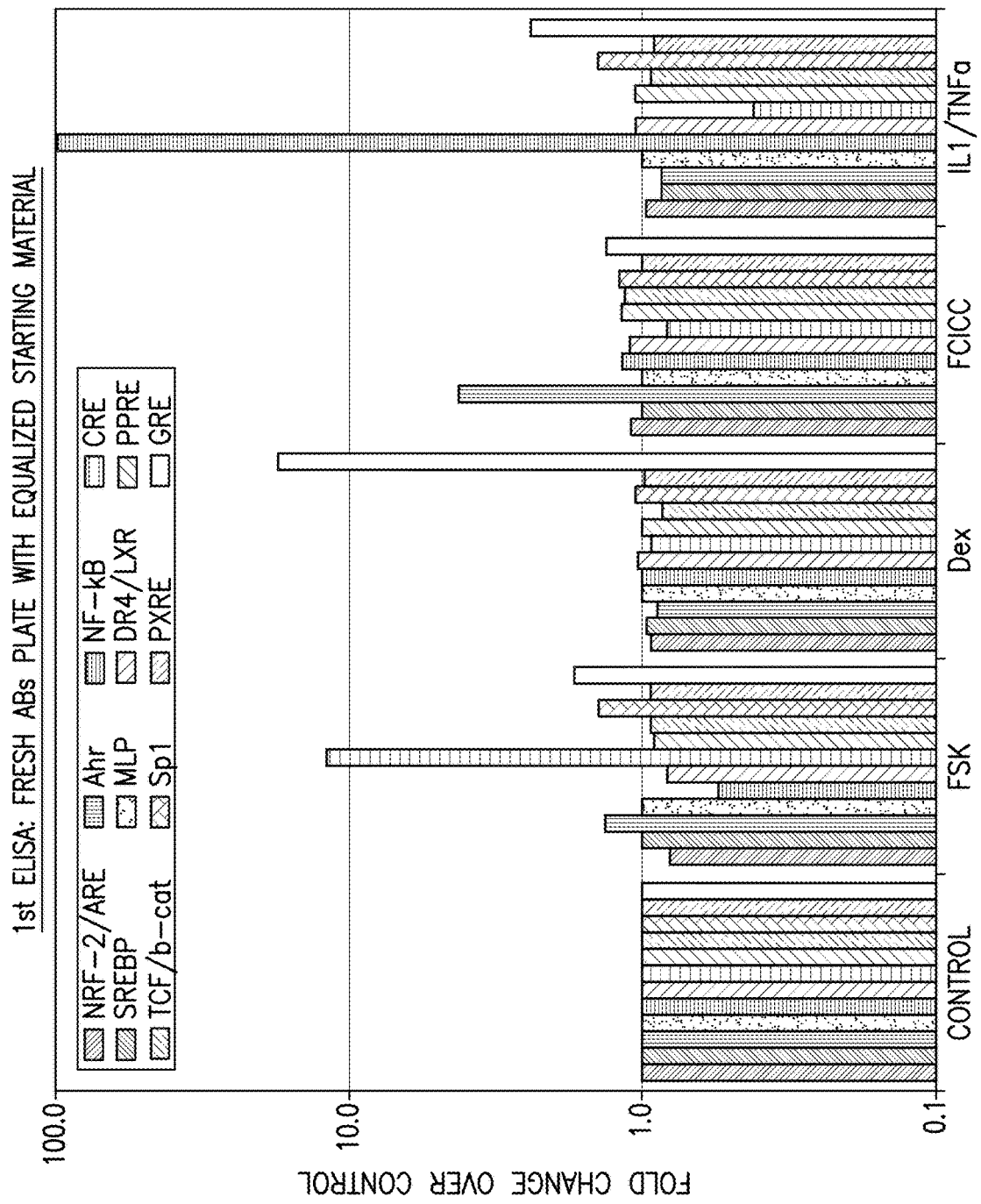

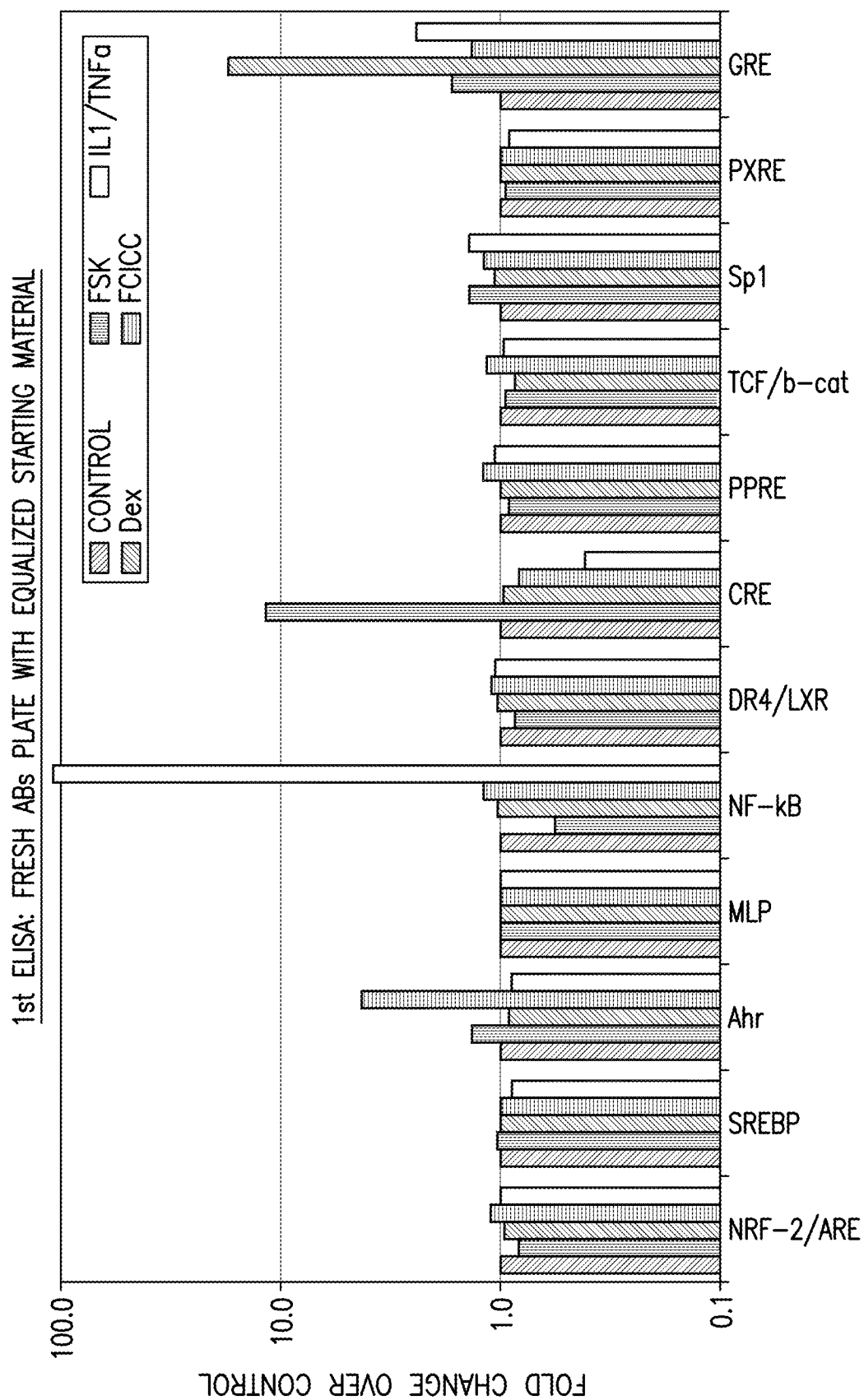

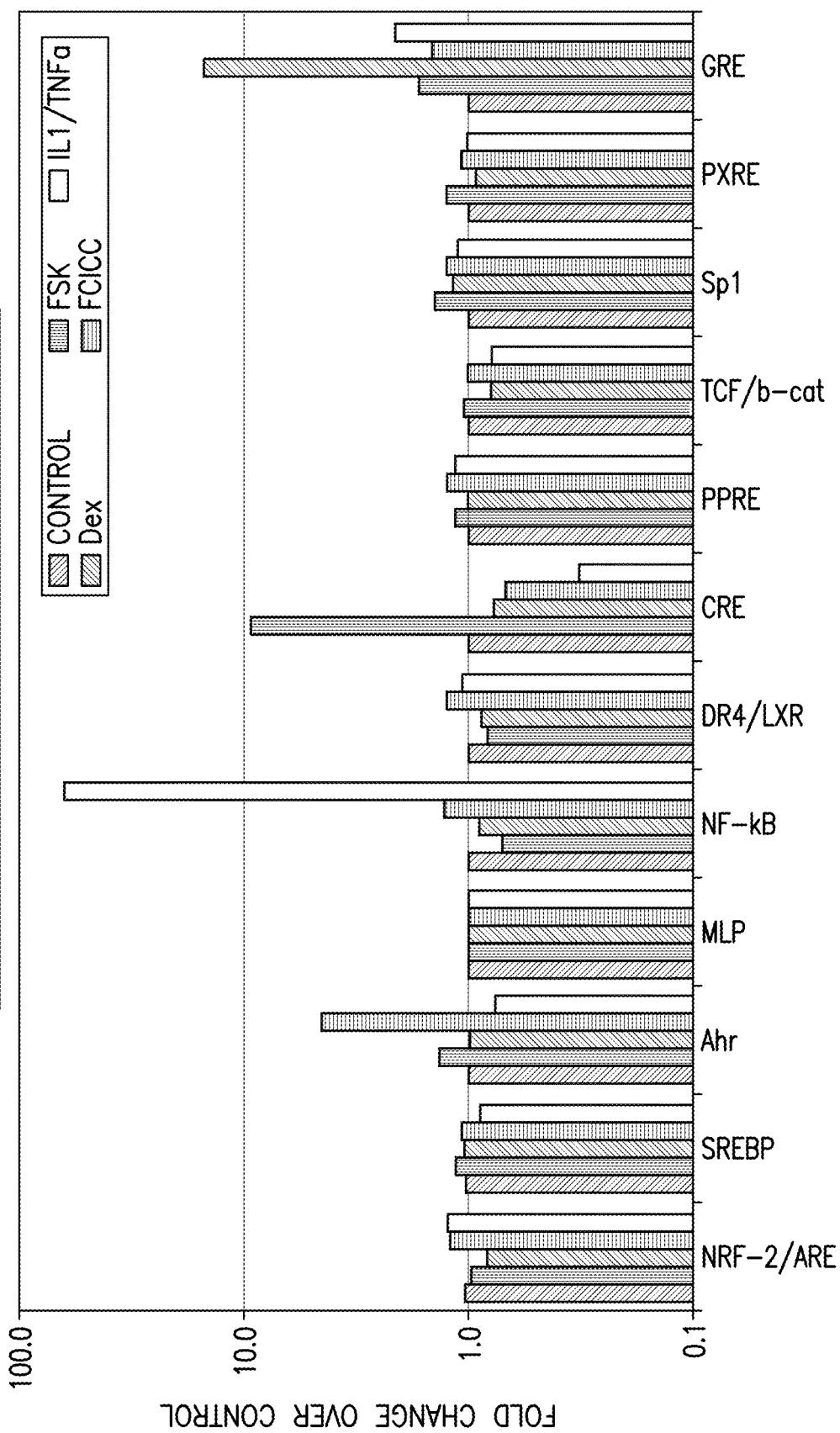

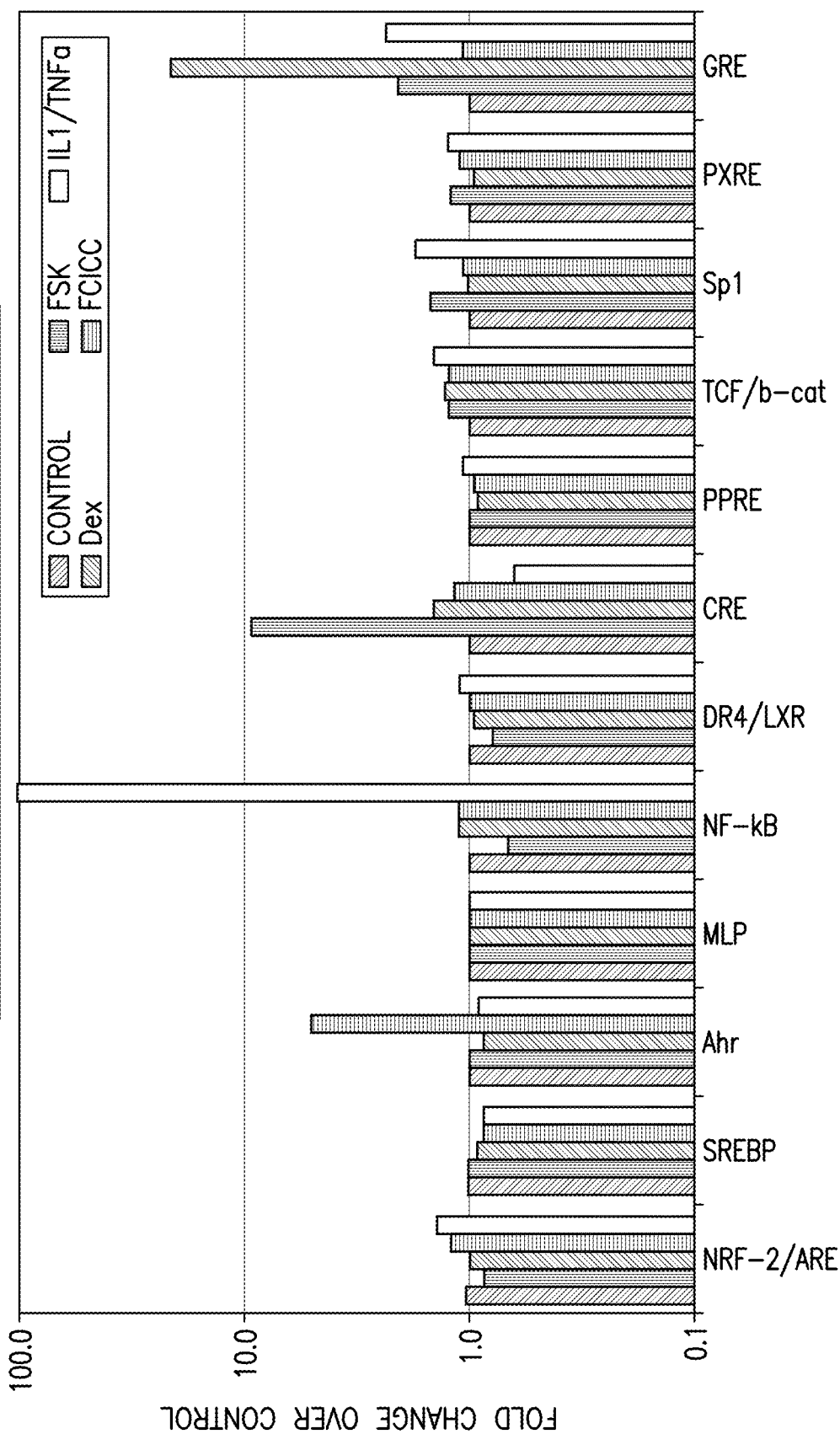

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Protein reporter system recognition region tag

<400> SEQUENCE: 1

His Thr Thr Pro His His
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: octapeptide marker tag

<400> SEQUENCE: 2

Asp Tyr Lys Asp Asp Asp Asp Lys
1               5

<210> SEQ ID NO 3
<211> LENGTH: 7
<212> TYPE: PRT
<213> ORGANISM: Artificial Sequence
<220> FEATURE:
<223> OTHER INFORMATION: heptapeptide marker tag

<400> SEQUENCE: 3

His Asn His Arg His Lys His
1               5
```

US 10,544,472 B2

MULTIPLEXING TRANSCRIPTION FACTOR REPORTER PROTEIN ASSAY PROCESS AND SYSTEM

CROSS-REFERENCE TO RELATED APPLICATION

This application is a U.S. national phase under the provisions of 35 U.S.C. § 371 of International Patent Application No. PCT/US15/10724 filed Jan. 9, 2015, which in turn claims the benefit under 35 U.S.C. 119 of U.S. Provisional Patent Application No. 61/929,043 filed Jan. 18, 2014 in the names of Sergei S. Makarov and Ming Zheng for "MULTIPLEXING TRANSCRIPTION FACTOR REPORTER PROTEIN ASSAY PROCESS AND SYSTEM". The disclosures of such International Patent Application and U.S. provisional patent application are hereby incorporated by reference in their respective entireties, for all purposes.

FIELD

The present disclosure relates to multiplexing reporter systems useful in simultaneous quantitative assessment of the activity of one or more transcription factors. The reporter systems include individual reporters, sets of reporters and libraries of reporters, each useful in assay methods of the disclosure.

DESCRIPTION OF THE RELATED ART

In gene transcription, expression of genes is regulated by a network of signal transduction pathways that culminate in the action of transcription factors (TFs), DNA-binding proteins that recognize specific sequences within regulatory regions of target genes and thereby modulate their transcription. It has been estimated that as many as 2000 transcription factors are encoded in mammalian genomes. TFs can be classified according to structural similarities of their DNA-binding domains. This classification results in 100 to 200 TF families with relatively constrained DNA-binding specificities of TFs within each family. By analyzing activities of the multiple TFs one can obtain an informative snapshot of the functional state of the entire gene regulatory network.

The activity of a TF is defined as its ability to activate or suppress gene transcription. In general, simple measurement of TF protein expression is not sufficient for determining its functional status. That is because many TFs can be present in the cell in an inactive state. Accordingly, in order to assess TF activity, additional markers should be evaluated.

As many TFs are regulated through modulation of their ability to bind DNA, DNA binding is often considered as a surrogate marker of TF activity. Many DNA-binding assays are presently available, including assays that can evaluate multiple TFs. However, while binding to the cognate DNA sequence is an essential step of TF regulation, its functional outcome may further depend upon additional regulatory events, such as protein modifications, as well as physical interactions with transcriptional co-repressors and co-activators. For example, many TFs that belong to a family of hormone nuclear receptors, i.e. retinoid and thyroid receptors, constitutively reside on their cognate DNA sequences, yet their transcriptional activity is strongly modulated through interaction with corresponding ligands. Therefore, DNA binding alone does not enable comprehensive functional TF assessments to be made.

A further approach for assessment of TF activity involves a reporter gene assay that makes use of a reporter gene construct, comprising a TF-responsive promoter that controls expression of a gene encoding a reporter protein. There are many well-characterized reporters, e.g., GFP (green fluorescent protein), RFP (red fluorescent protein), FLuc (Firefly Luciferase), RLuc (Renilla Luciferase), and AP (alkaline phosphatase), which have been utilized extensively in single reporter systems. However, using a single reporter system to analyze activities of multiple TFs in the entire gene regulatory network is tedious and nearly impossible, since maintaining identical conditions for hundreds or thousands of wells is difficult to achieve.

Alternatively, a multi-reporter system may be employed in assessment of TF activity, but such a system has its own technical challenges. It would be impossible to obtain a large number of similar reporters naturally. Since every reporter has a unique genetic background and maturation path, each is likely to differ in transcription, translation, post-translation modification, stability, and other regulations. Additionally, every reporter has its own optimal assessment method; it is impossible to find a uniform and sensitive assay for all of them. Various reporters can vary so dramatically that it will be impossible to compare them line by line to draw any convincing conclusion.

A cursory comparison of GFP and RFP, both fluorescent proteins, demonstrates how reporters can vary from one another. GFP is a monomer and matures within 12 hours, while RFP is a tetramer and requires over 48 hours to fully mature. The solubility and cyto-toxicity of these two peptides also differ significantly. Assays using these two reporters will not provide any reliable or directly comparable results, particularly in examination of two different TF response elements if they are constructed with GFP and RFP reporters, respectively. Therefore, the application of dual/triple reporter systems is mainly limited to use in transfection normalization among different wells driven under the same promoter. Since these reporters cannot be used simultaneously to quantify the activities of different TF response elements, this kind of dual/triple reporter system is not a true multiplexing reporter system. In addition, the degree of multiplexing in such system is low and it is barely possible to achieve utility with even three reporters.

There therefore remains a need in the art for a true multiplexing reporter system for assays of TF activity. The present disclosure provides such a system containing newly developed reporters. Use of such reporters in multiplexed assays of TF activity, as described herein, provides the advantages of extraordinary repeatability, accuracy, and robustness of the multiplexing assay. The multiplexed system of the disclosure provides the additional advantage of enabling direct assessment of quantitative information regarding enzymatic activity of the reporters and, correspondingly, of TF activity.

SUMMARY

The present disclosure relates to multiplexed protein reporter systems for simultaneous quantitative assessments of multiple transcription factors. The disclosure also relates to methods of using such systems and the reporters of such systems.

In one aspect, the disclosure relates to a protein reporter system for the simultaneous quantitative assessment of the activity of two or more transcription factors. Such system includes a set of two or more reporters, wherein each reporter comprises: a response element responsive to binding of a transcription factor; a backbone comprising a secreted enzyme; and a recognition region, fused to the C-terminal end of the backbone. The recognition region comprises a tag. The tag in various specific embodiments can alternatively comprise, consist of, or consist essentially of, 5 to 15 amino acids. In the protein reporter system, the recognition region of each reporter differs from the recognition region of any other reporter in the set.

In another aspect, the disclosure relates to a method for assaying activity of one or more transcription factors. The assay method comprises (a) culturing a sample containing one or more transcription factors with a set of two or more reporter gene constructs, each construct encoding a protein reporter comprising: a response element responsive to binding of a transcription factor; a backbone comprising an open reading frame of a secreted enzyme; and a recognition region, fused to the C-terminal end of the backbone, wherein the recognition region comprises a tag. The tag as indicated above may in various specific embodiments comprise, consist of, or consist essentially of, 5 to 15 amino acids. The recognition region of each protein reporter in the set differs from the recognition region of any other protein reporter in the set. The culturing is carried out under conditions sufficient to induce expression of the protein reporters, if the response element is bound by a transcription factor. The assay method additionally comprises (b) obtaining a sample of the supernatant of the culture, (c) contacting the sample of supernatant with a binding agent that is specific for the recognition region of a protein reporter of the set, and (d) quantifying the enzymatic activity of the reporter bound by the binding agent.

In a further aspect, the disclosure relates to a method for assaying activity of one or more transcription factors in an organ of an animal, such method comprising:
 (a) transfecting the organ of the animal, containing one or more transcription factors, with a set of two or more reporter gene constructs, each construct encoding a protein reporter comprising:
  a response element responsive to binding of a transcription factor;
  a backbone comprising an open reading frame of a secreted enzyme; and
  a recognition region, fused to the C-terminal end of the backbone, wherein the recognition region of protein each reporter differs from the recognition region of any other protein reporter in the set,
 wherein expression of the protein reporters is induced in the organ, if the response element is bound by a transcription factor;
 (b) extracting from the animal a sample of tissue of the organ or a biological fluid associated with the organ;
 (c) contacting the tissue or fluid with binding agent specific for the recognition region of a protein reporter of the set; and
 (d) quantifying the enzymatic activity of the reporter bound by the binding agent.

In a further aspect, the disclosure relates to a population of reporter constructs constituted for expression of the protein reporter system of the present disclosure.

A further aspect of the disclosure relates to a library of reporter constructs, in which each construct contains a promoter functionally linked to a reporter system so as to control transcription of a reporter sequence, each reporter in the library being identical except for a sequencing tag enabling identification of reporter sequences within the library by sequencing, wherein the sequencing tag comprises a substitution of one or several nucleotides in a tag sequence of the reporter.

In another aspect, the disclosure relates to a process of multiplexed detection of promoter activities of a library of reporter constructs of the present disclosure, such process comprising introducing the library of reporter constructs into a cell system to be evaluated, reverse transcribing transcribed reporter RNA expressed by the reporter constructs to yield reporter cDNAs, amplifying and sequencing the reporter cDNAs, determining activity of reporter constructs of the library by the number of cDNAs transcribed by the reporter constructs, by assessing numbers of reporter cDNAs containing the sequencing tag at a defined position, and determining activities of reporter constructs within the evaluated cell system by calculation of the ratio of reporter cDNAs transcribed by each reporter construct of the library.

Yet another aspect of the disclosure relates to a process for multiplexed detection of reporter constructs in multiple cell systems, comprising transfecting a reporter construct library into one or more evaluated cell systems, amplifying and sequencing reporter cDNAs in each evaluated cell system, determining activities of a given reporter construct in a given evaluated cell system by determining a number of cDNAs containing an identifier sequence tag and the sequencing tag at a defined position, and determining a profile of reporter construct activities in the evaluated cell systems by calculating cDNAs transcribed by each reporter construct within evaluated cell systems by counting reporter cDNAs containing the sequencing tags at defined positions and the identifier tags.

Other aspects, features and embodiments of the disclosure will be more fully apparent from the ensuing description and appended claims.

BRIEF DESCRIPTION OF THE DRAWINGS

FIGS. 2B-2D are graphs illustrating the effects of FBS buffer and BSA on the Glu-6×His reporter.

FIGS. 3A-3D are graphs illustrating the stability of the Glu-6×His reporter in different reagents (3A), and the Km of purified Glu-6×His in coelenterazine (3B), and the stability in different buffers (3C), as compared to a mixture of multiple Gluc-tags (3D).

FIGS. 4A-C are graphs illustrating the dynamic range of the Gluc reporter assay.

FIG. 5B is a graph illustrating the specificity of antibody binding to its respective tag on each of seven Gluc reporters.

FIG. 6B is a graph illustrating induced expression of Gluc reporters by various inducers over time.

FIGS. 8A-D are graphs illustrating the results of 4 assays with different input signals on different antibody plates; FIGS. 8A and 8B provide the results from assays performed with every well having a similar total RLU from different experiments; FIGS. 8C and 8D provide the results from assays performed with different total RLU but same dilution as the original induction experiments, where 8A and 8D used the same batch of antibodies, 8B used less antibodies and 8C has the least antibodies.

FIGS. 12A-D are graphs illustrating the induction fold change results of 4 assays with different input signals on different antibody plates; FIGS. 12A and 12B provide the results from assays performed with every well having a similar total RLU from different experiments; FIGS. 12C and 12D provide the results from assays performed with different total RLU but same dilution as the original induction experiments, where 12A and 12D used the same batch of antibodies, 12B used less antibodies and 12C has the least antibodies.

DETAILED DESCRIPTION

Figure 1A:
FIG. 1A is an illustration of an exemplary reporter of the invention.

The present disclosure relates to multiplexing protein reporter systems for use in simultaneous quantitative assessments of activities of multiple transcription factors. These high-capacity reporter systems overcome the limitations of previous approaches using traditional single reporter or limited dual/triple reporter systems.

A system of the present disclosure contains a developed set of reporters in which each reporter has a common structure and differs from other reporters in the set, e.g., by a few amino acids, preferably from 5 to 15 amino acids, at the C-terminus of the reporter. Each set of reporters contains a response element driven by a particular TF. In use of reporter systems of the disclosure, a library of reporter sets, each containing a different response element, with each set driven under a different TF, is provided. Subsequent to induction of the response elements, individual reporters are captured by a binding agent, e.g., an antibody or aptamer, that is specific to the reporter's unique tag and the reporters are directly quantified by the reporter's own enzymatic activities. Because of the common structure of all reporters in the set or library, the enzymatic activities are the same for all reporters in the set or library. This homogeneity of reporters brings about an inherent uniformity of individual assessments, thereby enabling an extraordinary repeatability, accuracy, and robustness in multiplexing assays to be achieved.

The disclosure further relates to the individual reporters, sets of such reporters and libraries of such reporters developed for use in such multiplexing systems. The sets and libraries of reporters include multiple reporters with similar properties in order to achieve a true multiplexing detection in such systems.

Development of protein microarray detection systems has lagged far behind the development of gene detection systems, in which hundreds or thousands of genes per chip are routinely employed. High throughput protein screening has been hindered by the lack of any practical and efficient way to perform such screening quickly and accurately. Current throughput for protein microarrays is limited to a range of 8-16 targets per well. It is difficult as a practical matter to detect and quantify vast amounts of various proteins with highly diverse sequences and structures at an acceptable accuracy and specificity. Conventional multiple protein detecting systems require an antibody for each target in order to achieve extremely high specificity and strong binding efficiency. The antibodies will only react with the particular targeted protein but not with any other protein in the mixture. Conventional multiple protein detecting systems also require two sets of antibodies (capturing and detecting (e.g. RFP, GFP, etc.)) for every target that are from different animal origins to avoid the nonspecific binding by the secondary antibodies, and the detecting antibodies have to be from the same animal source in order to realize a unified detecting procedure. With an increasing number of targets placed on the detecting list, the fabrication and operation of multiple protein detecting systems will become more and more challenging with time.

There are a number of reasons for the inefficiency of multiple native peptide quantification techniques. First, proteins are much more complicated than nucleic acids. Second, the quantification of proteins mainly relies on the availability of specific antibodies and a secondary labeling system, while very often the only antibodies available for certain targets are non-sensitive or low-sensitivity antibodies with high cross-activities. Third, a mix of a large amount of proteins at various abundances also poses a challenge to the system's ability to detect low-sensitivity antibodies and to avoid underestimation of high sensitivity antibodies. When combined with large differences in the binding efficiency of the pulling/detecting antibodies, this becomes an even bigger hurdle. Therefore, the targeted proteins have to be divided into much smaller subgroups, so that cross-reactive antibodies are separated into different groups. The targets have to be clustered according to the abundance in the mixture and the binding efficiency of antibodies to avoid exceeding the detection limit, and clusters with different abundance have to be detected in different ways, such as detection of high abundance clusters with fluorescent techniques and low abundance clusters with luminescent techniques.

The requirement of high specificity must be met for both capturing and detecting antibodies. In addition, a secondary or tertiary labeling system may have to be integrated into the detection system to obtain a final readout signal. When taking all these multiple complicated steps together, the specificity, sensitivity and signal/background ratio of the detection system begin to suffer dramatically, and variations of final results among different experiments become too large to be acceptable. As a result, most antibody based assays can only be semi-quantitative at best.

The multiplexing system of the present disclosure makes full use of binding agents such as currently available antibodies with known haptens/epitopes, or aptamers of known binding character, and the detection procedure is focused on only a single protein. When direct quantitation of concentration or activity of native targets is replaced by measurement of multiplexed reporters' activities, all above issues related to multiple native proteins detection can be eliminated.

Although reporters have been used widely for study of promoter functions, limited multiple reporters have been used simultaneously in cells, mainly for normalization purposes. No true high degree multiplexing reporter systems have been previously utilized, because multiple uniformed reporters are not naturally available. The reporter systems described herein have overcome many drawbacks of other systems. First, there are minimal variations among tagged-reporters in a set or library in the multiplexing reporter system of the present disclosure; the reporters form a group of uniform reporters with similar characteristics. Second, in the multiplexing reporter system of the present disclosure, the extremely wide dynamic range of detection of reporters' enzymatic core domain provides freedom for profiling different components with various abundances within a broad window of dilution. Third, the unique design of using an enzyme as a target in the multiplexing reporter system of the present disclosure directly and dramatically reduces the nonspecific binding problems encountered in previous reporter systems.

The multiplexing reporter system of the present disclosure provides reporters for use in multiplexed assays, in which the reporters are useful in quantitative and simultaneous assessment of the activities of TFs. A reporter of the present disclosure has the general structure shown in FIG. 1A.

In the multiplexing reporter systems of the disclosure, the carrier/reporter section constitutes a backbone that does not vary in a set or library of reporters. The carrier is a secreted enzymatic reporter, and is generally exogenous to the source of the sample containing the one or more transcription factors.

A true multiplexing assay method requires recruiting/constructing a group of similar but different reporters having uniform properties in transfection/expression/stability/detection to ensure comparability among them. Protein tagging technology is used to trace the function of a protein without changing the property of the target itself. When combined with the reporter technology, it provides a new way to generate multiple reporters to satisfy the above criteria. While any effective reporter can be used, reporters that are easily obtained and quantified are preferred. Exemplary secreted enzymatic reporters useful as backbones of reporters of the present disclosure include, without limitation, Gaussia luciferase (Gluc) and secreted embryonic alkaline phosphatase (SEAP). Both enzymes have fast maturing time, can be easily obtained and can be quantified by noninvasive methods from a culture supernatant, as described more fully herein. In addition, multiple time points of analysis are possible from a same batch of cell culture.

The stability of Gluc makes it an excellent selection for the backbone of reporters useful in the multiplexing reporter systems of the present disclosure. Gluc can be stably stored at 4° C. in medium supernatant or other buffers, with no diminution of activity for periods in excess of one year, if contamination is avoided. This stability of activity makes a Gluc enzyme assay time-insensitive, so that the assay can be done at any time after collection, with extremely high reproducibility of results.

A reporter of the present disclosure also includes a response element (RE). REs are binding sites for transcription factors. The transcription factor binds to the response element and induces a gene response. By inclusion of an RE on the C-terminal end of the reporter, the resulting constructed reporter is "TF responsive." Response elements useful in reporters of the disclosure may include, without limitation, nuclear factor kappa-light-chain-enhancer of activated B cells (NF-kβ), peroxisome proliferator response elements (PPRE), ternary complex factor (TCF), pregnane X response element (PXRE), cAMP response element (CRE), NF-E2-related factor 2 (NRF-2), Major late promoter (MLP), Sterol-responsive element-binding protein (SREBP), direct repeat 4 (DR4), glucocorticoid response element (GRE), Specificity Protein 1 response element (Sp1), aryl hydrocarbon receptor (Ahr), liver X receptor (LXR), and antioxidant response element (ARE).

A reporter of the present disclosure also includes a tag, which is the fingerprint and/or signature domain of each individual reporter. Though the backbone may remain the same among different reporters, tags included on the C-terminus of the backbone can be varied to enable identification of individual reporters. Accordingly, the tags provide a "recognition region" on each reporter. Tags included in reporters of the present disclosure may be protein or peptide tags and may be any length necessary for recognition and binding by an antibody or aptamer that is specific for the recognition region. In various embodiments, the tags can be from about 5 to about 15 amino acids in length. Where the tag has 15 amino acids as a maximum length, the total number of different tags corresponding to such maximum length is theoretically on the order of $20^{15}$ to $3.3 \times 10^{19}$. In practice, any epitope/hapten sequence with adequate antibody or aptamer binding can be used as a tag. The commercial availability of monoclonal antibody libraries with known epitopes/haptens, and corresponding aptamer libraries of known binding character, enable selection of reporter tags and corresponding binding agents to be carried out readily and easily, and simple screening techniques can be employed to generate candidate reporter tags and antibodies or aptamers from them. Exemplary tags of the invention include, but are not limited to: 6×His, c-Myc, V5, FLAG™ octapeptide marker tag DYKDDDDK (SEQ ID NO: 2), HA, Glu-Glu, VSV-G, T7, S tag, protein C, MAT™ heptapeptide marker tag HNHRHKH (SEQ ID NO: 3), KT3, IRS, HTTPI-IH (SEQ ID NO: 1), HSV, B tag, AU1, and AU5.

Reporters of the present disclosure may be combined in any manner for use in methods of the disclosure. In one embodiment, a "set" of reporters is generated, where the RE and carrier of the reporter remain the same and the individual tags are varied. The following is an exemplary set of reporters of the invention:

RE-TATA-Gluc-6×His
RE-TATA-Gluc-c-Myc
RE-TATA-Gluc-V5
RE-TATA-Gluc-FLAG™ octapeptide marker tag DYKDDDDK (SEQ ID NO: 2)
RE-TATA-Gluc-HA
RE-TATA-Gluc-Glu-Glu
RE-TATA-Gluc-VSV-G
RE-TATA-Gluc-T7
RE-TATA-Gluc-S tag
RE-TATA-Gluc-MAT™ heptapeptide marker tag HNHRHKH (SEQ ID NO: 3)
RE-TATA-Gluc-KT3
RE-TATA-Gluc-IRS
RE-TATA-Gluc-HTTPHH (SEQ ID NO: 1)
RE-TATA-Gluc-HSV
RE-TATA-Gluc-B tag
RE-TATA-Gluc-AU1
RE-TATA-Gluc-AU5

A set of reporters may comprise as many individual members as there are tags to be utilized.

In a further embodiment, a "library" of reporters is generated, comprising two or more "sets" of reporters. In such libraries, the carrier of the reporter remains the same and both the RE and the individual tags are varied. The following is an exemplary library of reporters of the invention, containing both a NF-kβ set of reporters and a PPRE set of reporters:

NF-kβ-TATA-Gluc-6×His
NF-kβ-TATA-Gluc-c-Myc
NF-kβ-TATA-Gluc-V5
NF-kβ-TATA-Gluc-HSV
PPRE-TATA-Gluc-6×His
PPRE-TATA-Gluc-c-Myc
PPRE-TATA-Gluc-V5
PPRE-TATA-Gluc-HSV A library of reporters may comprise as many individual members as there are combinations of REs and tags to be utilized.

Potential unknown effects from multiple tags can affect the biological process to which the reporters are responding. This is a problem that can otherwise create some misleading results, but it is readily addressed by using two different libraries of tagged reporters for each response element (e.g., a combination of a Gluc library and a SEAP library). Different results from two libraries of tags will provide comparisons enabling analysis of the source of the effects. The following is an exemplary group of reporters of the invention for use in identification of such negative effects:

NF-kβ-TATA-Gluc-6×His
NF-kβ-TATA-Gluc-c-Myc
NF-kβ-TATA-Gluc-V5
NF-kβ-TATA-Gluc-HSV
PPRE-TATA-Gluc-6×His
PPRE-TATA-Gluc-c-Myc
PPRE-TATA-Gluc-V5
PPRE-TATA-Gluc-HSV
NF-kβ-TATA-SEAP-6×His
NF-kβ-TATA-SEAP-c-Myc
NF-kβ-TATA-SEAP-V5
NF-kβ-TATA-SEAP-HSV
PPRE-TATA-SEAP-6×His
PPRE-TATA-SEAP-c-Myc
PPRE-TATA-SEAP-V5
PPRE-TATA-SEAP-HSV Thus, in another embodiment, the disclosure provides methods for simultaneous quantitative assessment of the activity of one or more transcription factors, comprising use of the reporter systems of the disclosure. Assay methods of the disclosure can include the steps of: (a) culturing a sample containing one or more transcription factors with a set of two or more reporter gene constructs, each construct encoding a protein reporter comprising: a response element responsive to binding of a transcription factor; a backbone comprising an open reading frame of a secreted enzyme; and a recognition region, fused to the C-terminal end of the backbone, wherein the recognition region may for example be constituted as a tag of 5 to 15 amino acids, and wherein the recognition region of each protein reporter differs from the recognition region of any other protein reporter in the set, and the culturing is conducted under conditions sufficient to induce expression of the protein reporters, if the response element is bound by a transcription factor; (b) obtaining a sample of the supernatant of the culture; (c) contacting the sample of supernatant with binding agent, e.g., one or more antibodies or aptamers that are specific for the recognition region of a protein reporter of the set; and (d) quantifying the enzymatic activity of the reporter bound by the binding agent.

Assay methods of the invention may use individual reporters, sets of reporters, libraries of reporters, or any other grouping of reporters necessary to achieve optimal quantification.

The homogeneity of the reporter systems affords inherently uniform transfection and detection conditions for all reporters and therefore provides extraordinary repeatability, accuracy and robustness of assessments, with the small variations at the C-terminus providing a signature or fingerprint identity for each reporter. This system of reporter constructs can be easily introduced into the cells by transfection either individually or collectively. Since all reporters contain a common secreted enzymatic backbone domain, they can be captured and measured directly through a sensitive chemi-luminescent assay from the culture medium. Because there are no detecting and secondary antibodies or indirect labeling steps involved, the specificity and ratio of signal/background are dramatically improved, as compared to prior systems.

In another implementation, an assay method for assaying activity of one or more transcription factors may be carried out in an organ of an animal, e.g., a mammalian animal such as a mouse, rat, pig, or other animal. The organ of such animal, e.g., liver, spleen, kidney, etc., is transfected with the reporter gene constructs, and biological tissue of the organ, or biological fluid associated with such organ, e.g., blood, lymph fluid, etc., is extracted from the animal and contacted with the binding agent specific for the recognition region of the protein reporter following which the enzymatic activity of the reporter bound by the binding agent is quantified.

More specifically, such aspect of the disclosure may be carried out as a method for assaying activity of one or more transcription factors in an organ of an animal, in which the method comprises:
(a) transfecting the organ of the animal, containing one or more transcription factors, with a set of two or more reporter gene constructs, each construct encoding a protein reporter comprising:
a response element responsive to binding of a transcription factor;
a backbone comprising an open reading frame of a secreted enzyme; and
a recognition region, fused to the C-terminal end of the backbone, wherein the recognition region of protein each reporter differs from the recognition region of any other protein reporter in the set,
wherein expression of the protein reporters is induced in the organ, if the response element is bound by a transcription factor;
(b) extracting from the animal a sample of tissue of the organ or a biological fluid associated with the organ;
(c) contacting the tissue or fluid with binding agent specific for the recognition region of a protein reporter of the set; and
(d) quantifying the enzymatic activity of the reporter bound by the binding agent.

Unlike most indirect immunoassays with narrow assay ranges, the assay of the present disclosure has more than 8 magnitudes dynamic detection range with $R^2$ value>0.999, so multiple differently abundant reporters in the supernatant mixture can be quantified accurately by the reporters' own enzymatic activities. Due to the simplicity and the robust nature of this multiplexing system, it can be easily applied to any high throughput screening system to provide a systematic technique for drug screening and toxicity study. The multiplexing approach of the present disclosure is useful for identification of pathways transmitting cell responses to various inducers and provides a framework for functional characterization of signal transduction networks via profiling activities of multiple transcription factors, as well as providing a new tool to study genome-wise gene functions.

The reporter systems of the disclosure have been developed systematically, through observation and testing of individual characteristics and determination of optimal reporter structure and desired performance.

In this development effort, a reporter system with uniform features has been involved, utilizing the reporter structure shown in FIG. 1A. The response elements of interest are placed in front of the reporter/carrier's open reading frame (ORF) backbone and a tag is fused to the C-terminus of the reporter. Since all of reporters have same backbone and only differ from each other by relatively few amino acids at the C-terminus, their regulation and maturity should be similar. As a result, these reporters can be reliably compared on a line by line basis. On the other hand, because of the relatively small number of amino acids serving as its fingerprint, the tag will easily and reliably show every reporter's identity and the activity of the individual response element linked to a particular reporter. The combined features of uniformity and an individual fingerprint for each reporter permit a high degree multiplexing reporter system to be achieved.

Figure 1B:
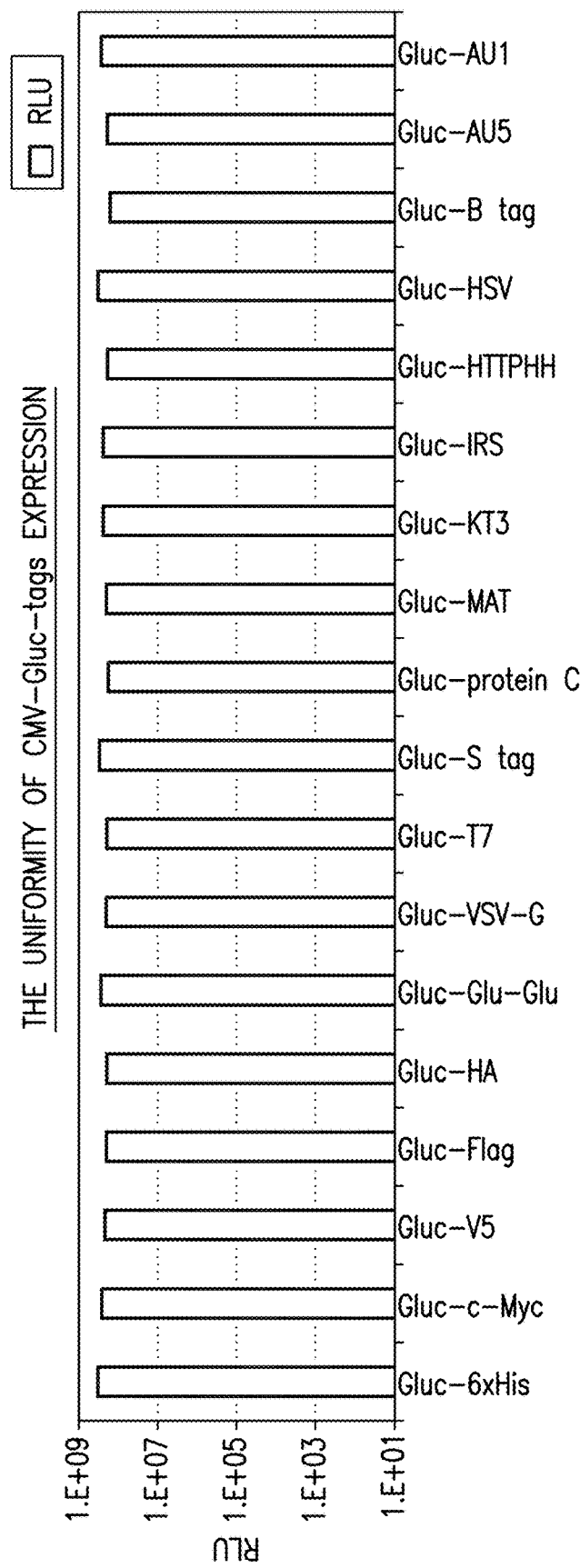
FIGS. 1B and 1C are graphs demonstrating expression by reporter systems using a Gluc (1B) or SEAP (1C) reporter backbone.
Figure 1C:
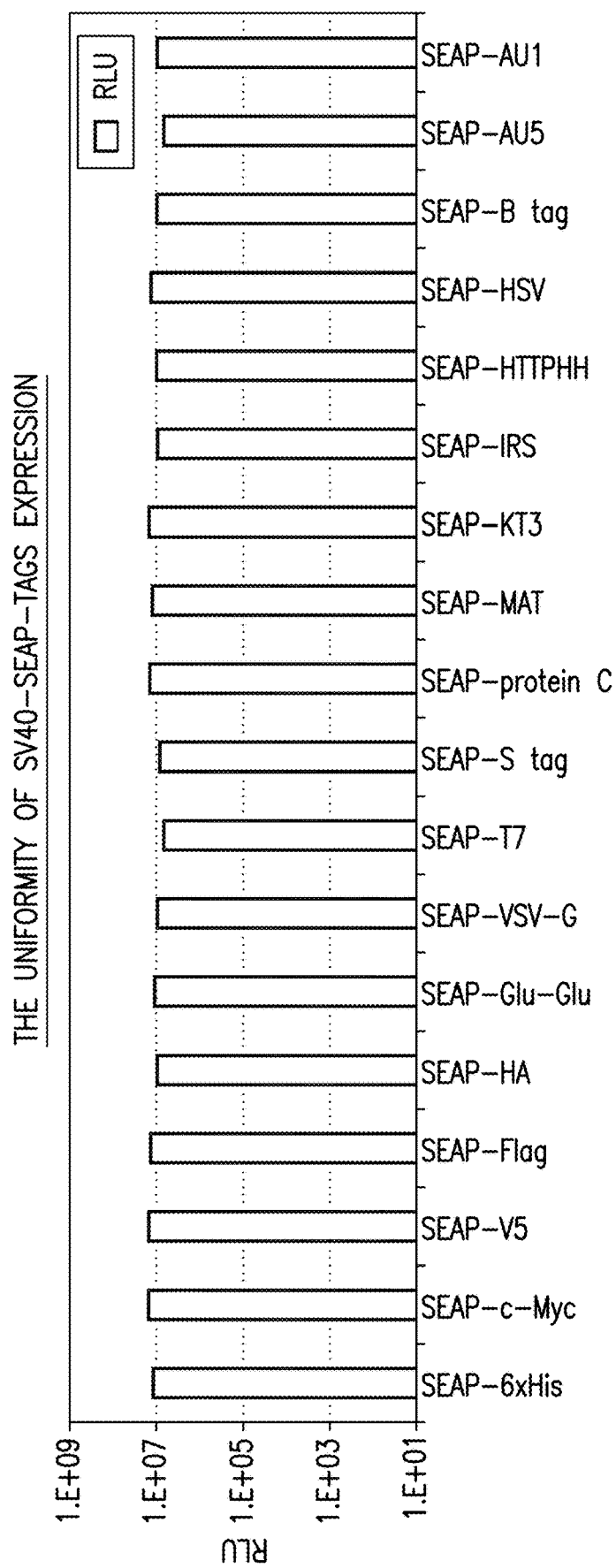

Both SEAP and Gluc are secreted proteins with high dynamic measuring range. SEAP is a 309 amino acids long peptide and Gluc is 170 amino acids long. Eighteen randomly chosen different tags were cloned and fused into the C-terminus of both Gluc and SEAP reporters and then expressed in 293H and HepG2 cells. As seen in FIGS. 1B and 1C, all reporters show very similar expression profile under the control of CMV promoter (Gluc) or SV40 promoter (SEAP). This demonstrates the utility of both Gluc and SEAP in a uniform reporter system. Gluc has been utilized to demonstrate the principles of such a multiplexing reporter system, because of its observed speed of expression and maturation, but other backbones, including but not limited to SEAP, can be utilized in other embodiments of the disclosure.

Gluc is a small protein with only 170 amino acids in its mature form. It also contains an additional 17 amino acid leading peptide in its N-terminus. It is a fast maturing peptide and does not require post-translational modification. As used in multiplexing systems of the present disclosure, Gluc was derived from a non-mammalian origin of the marine copepod Gaussia princeps and the open reading frame codes were humanized. The resulting protein is non-toxic and naturally secreted. Since most transcription factor studies are done in mammalian-originated culture systems, there are significant advantages of using this non-mammalian reporter in the system: 1) no background signal is elicited from the host cells; 2) the over-expressed reporters will not be accumulated inside of the hosts to cause toxic effects; 3) the Gluc reporter protein has no internal biological function in the mammalian cells, and therefore it will neither interfere with the host's normal physiological function nor create unexpected functional side effects from the remaining reporters inside the cells.

Figure 2A:
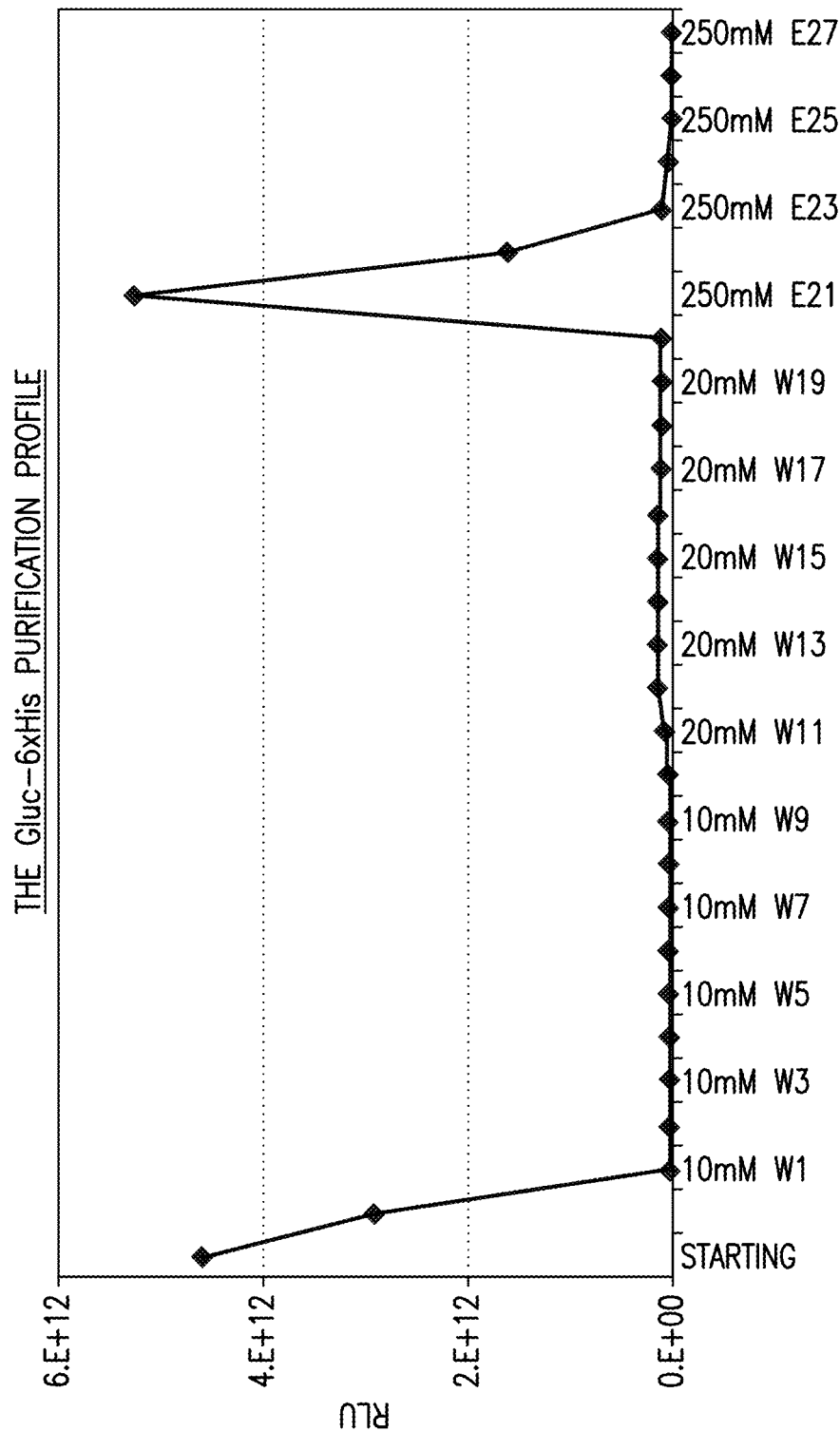
FIG. 2A is a graph of the purification of the Glu-6×His reporter.

To further assess the features of Gluc and its assay, this enzyme was purified from the culture supernatant of the 293H cells that over-expressed Gluc-6×His fusion protein. The profile of one-step purification of Gluc-His using the Ni-NTA Super-flow Columns (Qiagen, Valencia, Calif.) is shown in FIG. 2A. The majority of Gluc-6×His had bound to the column and the protein was effectively eluted with two bed volumes of 250 mM of Imidazole. As shown in FIG. 2A, the recovered activity is higher than the starting activity, indicating that there were inhibitory factor/factors present in the original culture supernatant.

Figure 2D:
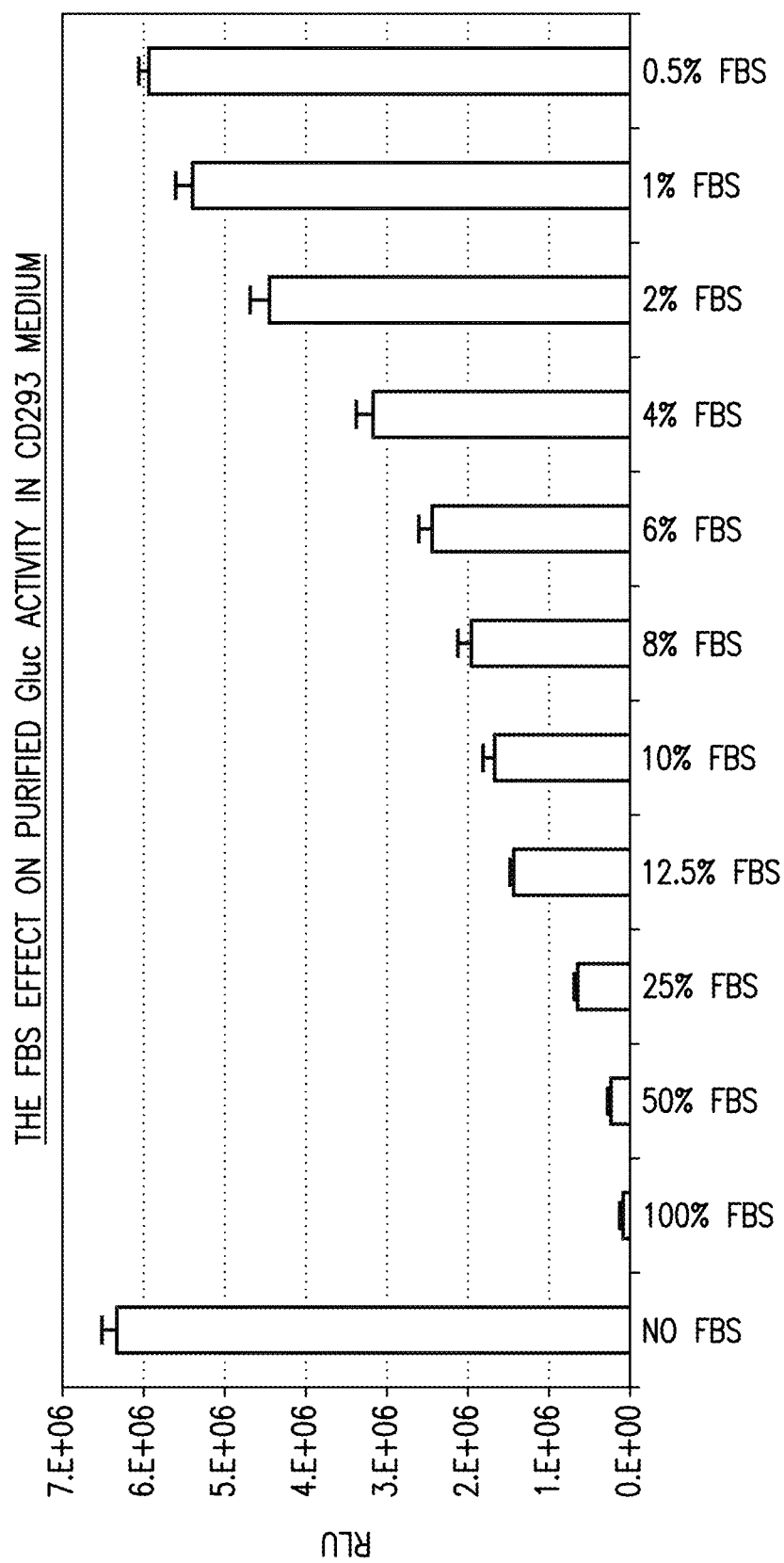

BSA (bovine serum albumin) is often used in buffers to protect enzyme activity from nonspecific binding and inactivation. The effects of BSA and FBS (fetal bovine serum) on Gluc activity were tested. The inhibition effect from BSA Fraction V (Roche; Basel, Switzerland) and FBS (Hyclone; Logan, Utah) can be seen in FIGS. 2B and 2C. The true inhibitor can be BSA itself or other components in the serum that coexist in the Fraction V of BSA. Interestingly, the low amount of FBS in the buffer (<10%, equivalent of <0.5% BSA) had some boosting effects, which can be explained as relating to the protecting effect (from the nonspecific absorbing and inactivation) being larger than the inhibition effect at low concentration. The FBS inhibition can be seen even at low concentration in other buffers containing protecting reagents, such as Invitrogen's CD293 medium (FIG. 2D).

The assay buffers from different vendors were compared and the commercially available assay stabilizer was tested. The RLU readout was about ten times higher from the Attagene assay reagent (Attagene, Inc., Research Triangle Park, N.C.) than from the other two commercial reagents under the same assay condition (FIG. 3A). The overlapping curves of NEB (Ipswich, Mass.) and Nanolight Technology (Pinetop, Ariz.) indicated that these two buffers may have a same formula. The stabilizer from Nanolight reduced the initial signal output by about 1000 times and the signal output was still significantly lower 40 minutes after the injection of substrate. Since the reading integration time was only a few seconds after the injection, it was not desirable or necessary to use stabilizer for the Gluc activity measurement, in view of the substantial sensitivity reduction attendant the use of the stabilizer. The $K_m$ (~20 uM) measurement curve for purified Gluc-His is shown in FIG. 3B. The $K_m$ value for raw Gluc material, as taken directly from the supernatant of transfected cell culture medium, was also tested and was found to be in the range of 30-40 uM (data not shown). Both purified Gluc and raw Gluc from the medium showed very good sensitivity, demonstrating that it is unnecessary to purify the Gluc from the culture medium before the measurement is made. This in turn makes the detection step much easier and robust in character.

Figure 3C:
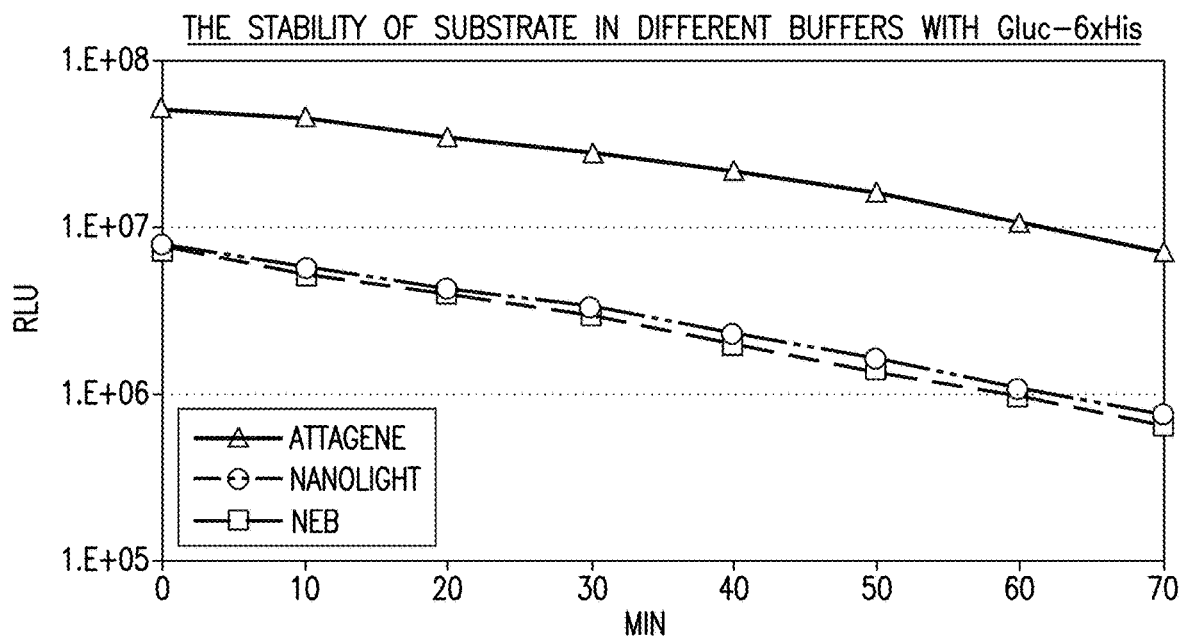
Figure 3D:
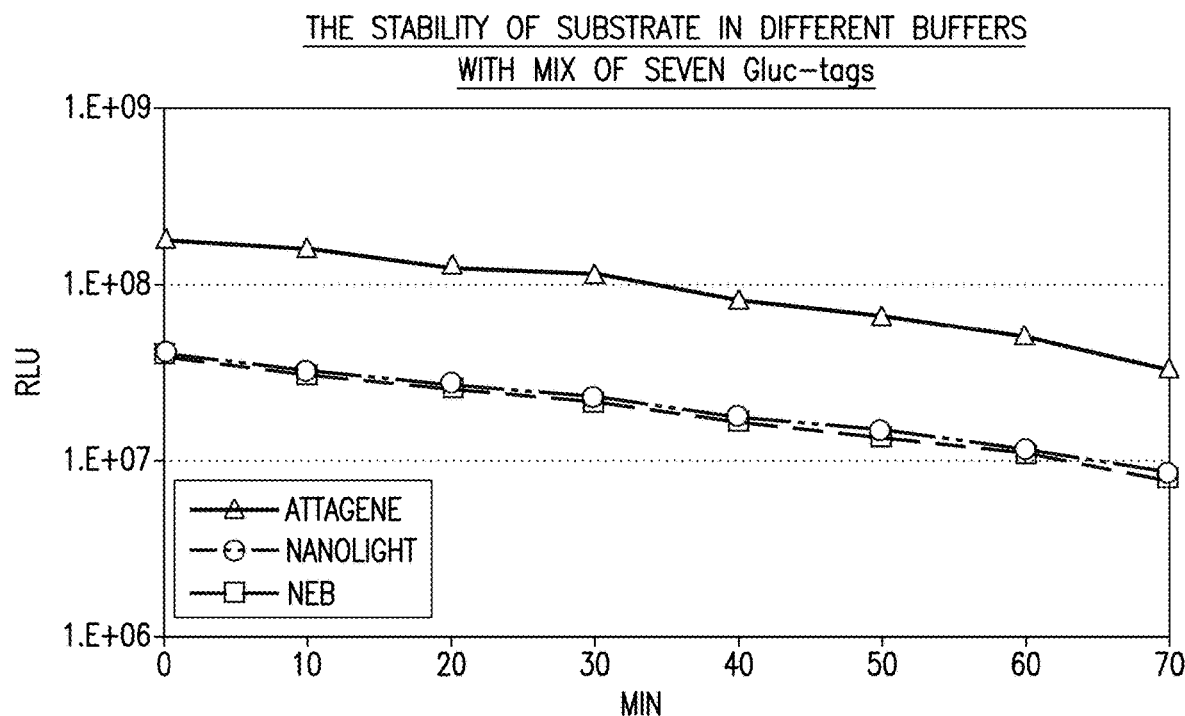

It is well known that coelenterazine is not stable in aqueous solutions. FIGS. 3C and 3D show the stability profiles of coelenterazine substrate in different assay reagents after being diluted from its methanol stock. A solution of Gluc enzyme was injected at different time points into substrates that were prepared at the same time. The overall signal strength decreased about ten times over 70 minutes and there was no significant difference among these buffers in the stability of the substrate. Once again, the Attagene reagent provided better sensitivity and stronger RLU output. There was no significant difference with either purified Gluc-6His or a mixture of multiple Gluc-tags, indicating that mixing of multiple tags was did not affect Gluc's enzymatic characteristics.

An examination of Gluc's dynamic range was used to determine the sensitivity of a reporter assay using Gluc and the tolerance to abundance differences among reporters. The typical dynamic range for a transcription factor assay is about 2-3 magnitudes. As shown in FIGS. 4A and 4B, at both of 5 µM and 20 µM substrate concentrations, more than 8 magnitudes of log range with $R^2$ value>0.999 were achieved with the Gluc assay when it was diluted in the binding buffer. The high limit was due to the maximal physical reading capacity of the Veritas Microplate Luminometer (Turner Biosystems, Sunnyvale, Calif.) used in the assay, and the low limit extended to the fento gram range.

Figure 4C:
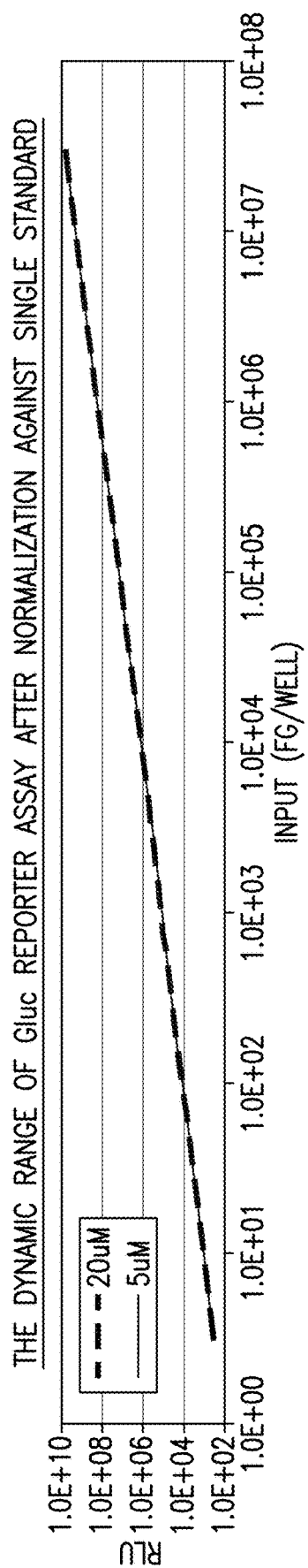

As discussed previously, coelenterazine was not stable in aqueous buffers. This makes it very hard to control the accuracy of the substrate concentration at the time of the assay. Luminometer preparation, the number of samples tested, and different operators, were all factors causing differences in final substrate concentration. This can be a significant issue in cross-comparing RLU readouts of the same samples assayed at different times, the data sets from different plates, or the results of different experiments conducted at different points in time. In FIG. 4B, two separate assays were conducted at different points in time. A common standard at only one concentration was included in both assays. The RLU readout was very different for assays using 20 uM and 5 uM of substrate before the normalization, but the final results were remarkably similar, as shown in FIG. 4C, when normalized against the common standard. Although these two sets of substrates and enzyme serial dilutions were done at different times, after being normalized against the same standard, the results overlapped across eight entire magnitudes. This is due to a nearly perfect wide dynamic linear assay range, which makes it unnecessary to do full standard curves each time an assay is conducted, since a single concentration of the standard is sufficient for normalization.

Immunodetection of targets by antibodies has been widely used in many areas of biotechnology. Western blot, RIA (radio-immuno assay), IHCA (immuno-histochemistry assay), IFA (immuno-fluorescent assay), IP (immuno-precipitation assay) and ELISA (enzyme linked immuno-sorbent assay) are all antibody-based assays. Some serve for quality assays with yes/no results, and some serve for semi-quantitative assays, but very few are quantitative; some are used as direct assays, some are used as indirect assays by linking with secondary labeling systems, such as enzymes, fluorescent or radioactive signals, and some even need a tertiary labeling step to amplify the signals.

There are many problems commonly associated with antibody-based assays, which include narrow assay dynamic ranges, multiple complicated labeling steps for indirect secondary or tertiary labeling systems, low signal strength, high background generated from nonspecific binding and multiple-step labeling of antibodies.

Figure 5A:
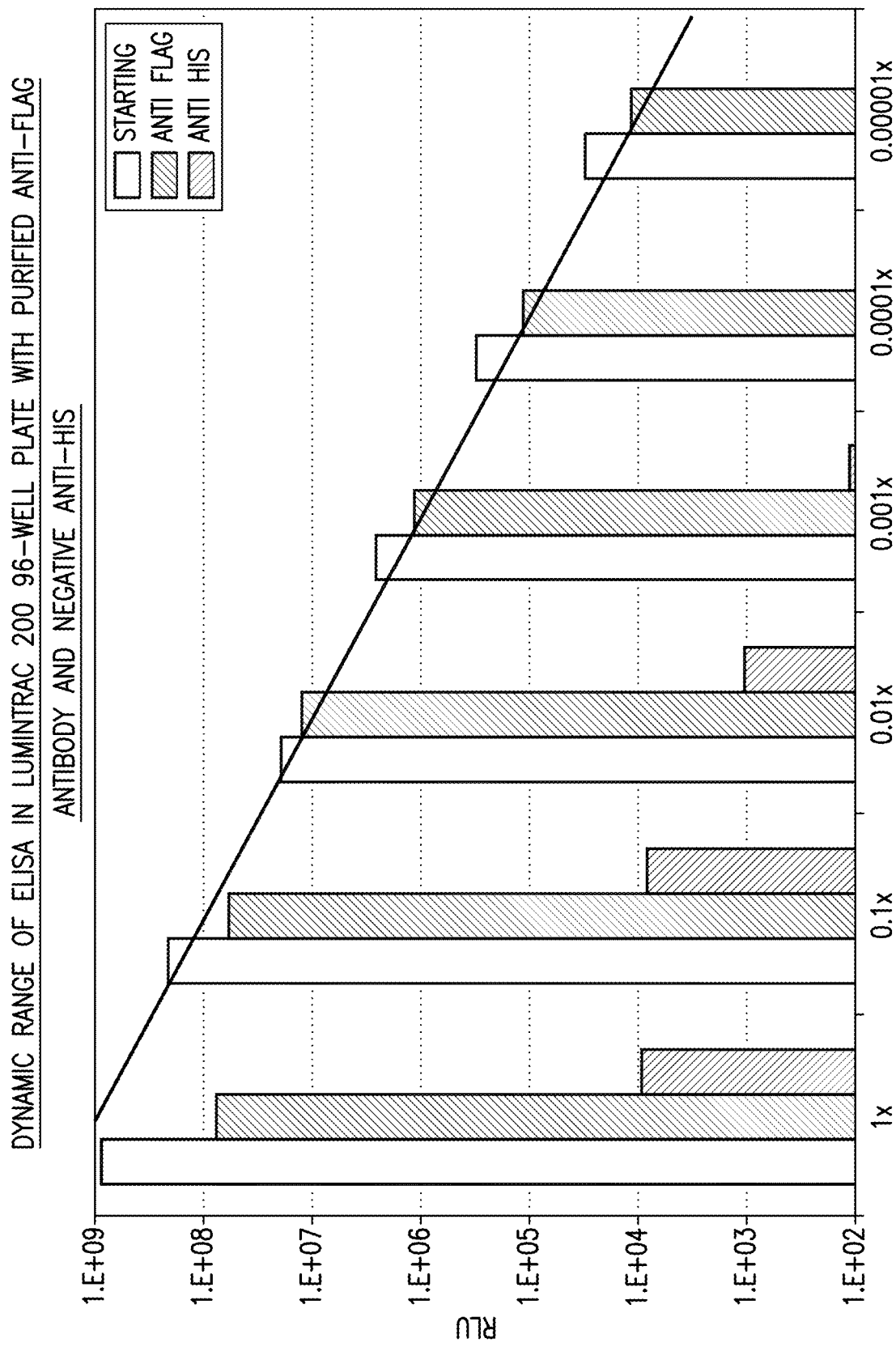
FIG. 5A is a graph illustrating the results of the binding and assaying of FLAG™ octapeptide marker tag DYKDDDDK (SEQ ID NO: 2)-tagged Gluc by its antibody.

The utility of immunoassays can be greatly improved if binding, labeling and assaying are all combined in a single step. This is achieved by the assay system of the present disclosure, e.g., when sensitive tagged Gluc having a wide dynamic range is used in the system. The supernatant from the culture medium containing tagged Gluc is simply and easily applied to a pre-formatted antibodies bound plate. After a brief incubation and washing step, results are readily obtained by injecting the substrate directly into the wells. No additional detecting and secondary antibody binding or other labeling steps are needed. The simple detection step procedure of the present assay provides more accurate and reliable results, since less distortive manipulations are involved. The binding and assaying of flag tagged Gluc by its antibody is shown in FIG. 5A, demonstrating that such assay has a very extensive dynamic range. The antibody accurately reflected the input of Gluc FLAG™ octapeptide marker tag DYKDDDDK (SEQ ID NO: 2) for 5 magnitudes with signal/noise ratio greater than 1000, being limited only by close approach to its maximal binding capacity. These results indicate that antibody can be used to accurately quantify the input of Gluc-tags from culture supernatant, thereby enabling high throughput profiling by the multiplexed reporter system. Similar results were obtained with SEAP-tags.

The profile of the assay's specificity for seven antibodies is shown in FIG. 5B. The sources of antibodies, the antibody purification methods, the antibody/antigen interactions, and the ways that the antibody is blotted, are all factors that will affect their binding capacity/affinity properties. Although the binding capacities/affinities are quite different among these antibodies, only the particular Gluc-tag reacted with its own specific antibody. The desired binding capacity can be achieved by generating and screening antibodies to identify those with the corresponding binding characteristics. In the corresponding use of aptamers as binding agents, corresponding screening is carried out, but in many applications of the assay system and method of the present disclosure, antibody binding agents will be preferred.

There are several factors that contribute to the unusual specificity of the assay system of the present disclosure: 1) Gluc is a foreign-originated marine copepod protein, and therefore does not have much cross-activity with the naturally-occurring antibodies in a mammalian system; 2) the cross-reactivity region is limited to the short tag sequences, making such cross reaction much less likely to happen. 3) the tolerance of nonspecific binding is very high. By using a sensitive enzyme reporter directly without a secondary labeling step, the sensitivity and ratio of signal and background have been dramatically improved. The reporter assay of the present disclosure also eliminates the stringent requirement of antibody specificity for detection and the secondary antibodies that are required in other immunoassays. The present assay is blind to any other type of nonspecific bindings as long as the pulling antibody does not react with other tags and reporter backbone domain. Since only specific tags, e.g., Gluc-tags, will contribute to the final readout and other types of binding will be silent in the results even if occurring, the reporter assay of the present disclosure provides a significant advantage over other antibody-based assays.

Figure 6A:
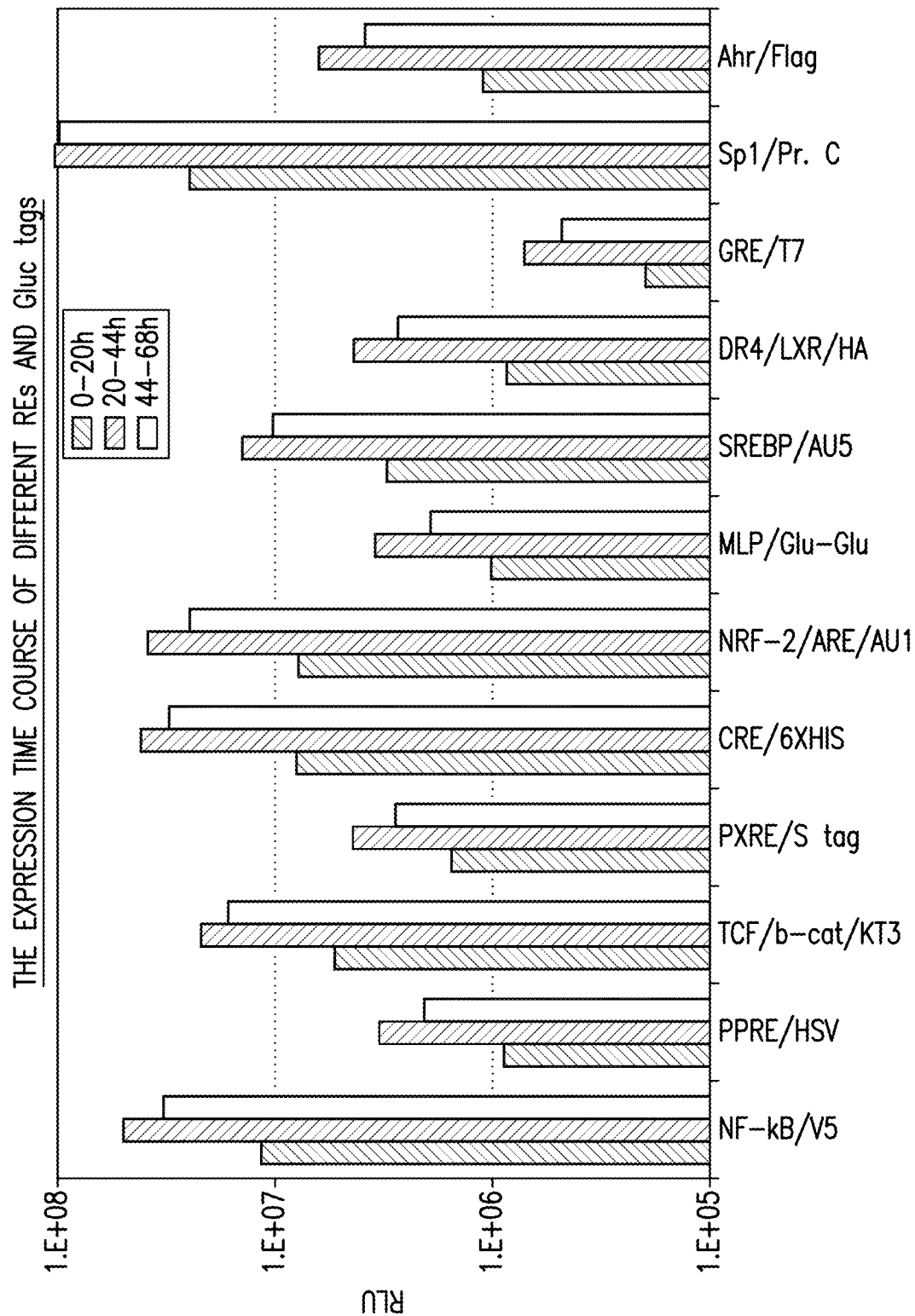
FIG. 6A is a graph illustrating the expression of 12 different reporters over various time intervals.

Subsequent to establishing the uniformity, sensitivity and specificity of Gluc-tag reporters, effective multiplexing was demonstrated for these reporters. As shown in FIG. 6A, the basal expression of 12 different response elements (REs) and their expression time courses are very different. The expression level of these RE driven Gluc-tags can vary over 100 times from low levels to high levels. This variability indicates the need for adjustments to balance the starting level by using different amounts of plasmid inputs in the mixture during transfection. The induction can be detected at as early as 2 hours after the addition of inducer (FIG. 6B). The speedy expression and maturing of Gluc make it particularly useful for tracing quick response inducers.

Figure 7A:
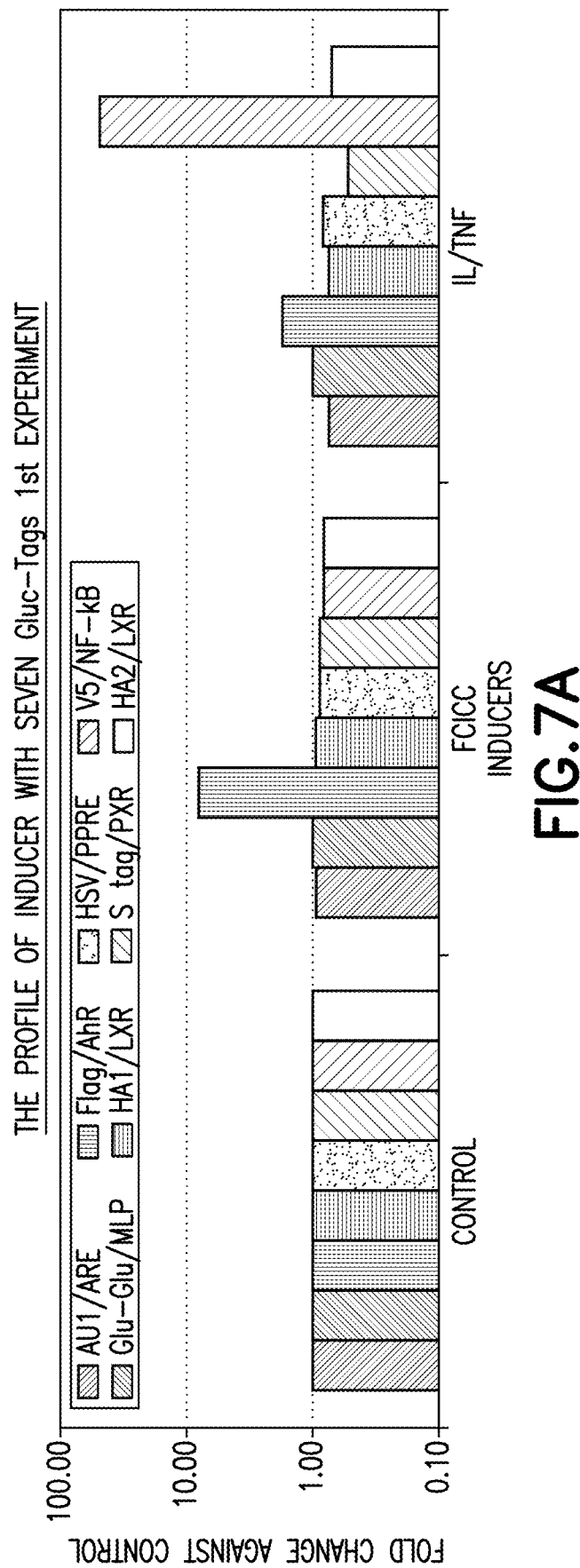
FIGS. 7A and 7B are graphs illustrating two experiments with 8 different reporters, in the presence of inducers FCICC, IL-1β and TNF-α.
Figure 7B:
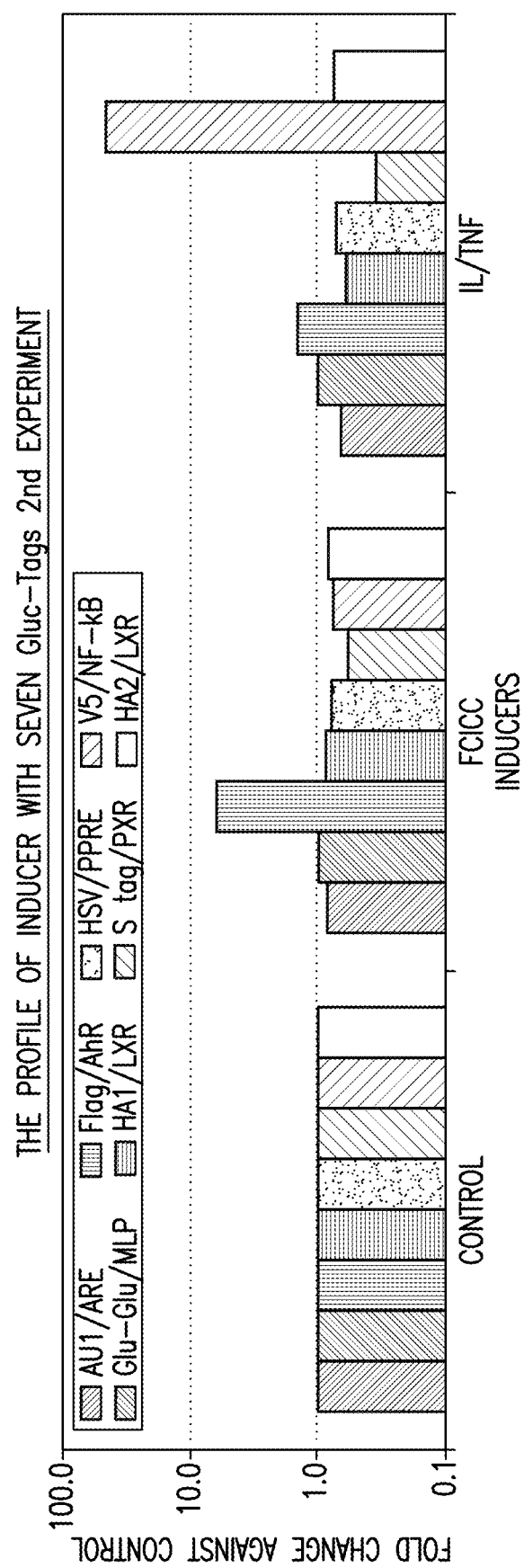

To demonstrate multiplexing capability, seven antibodies were blotted on 7 rows of a 96-well Lumintrac600 plate and one row served as a "no antibody" control. Two separate detection assays were conducted to check the profile of FCICC (6-Formylindolo [3, 2-b] carbazole Indolo [3,2-b] carbazole-6-carboxaldehyde-5, 11-dihydro, an AhR response element inducer, commercially available from Biomol, Plymouth Meeting, Pa.) and IL-1β and TNF-α (NF-κB response element inducer). There was no detectable binding to the "no antibody" control, but the assays showed very similar and specific induction of AhR (by FCICC) and NF-κB (by IL-1β and TNF-α) respectively, in these two experiments (FIGS. 7A and 7B).

Figure 8B:
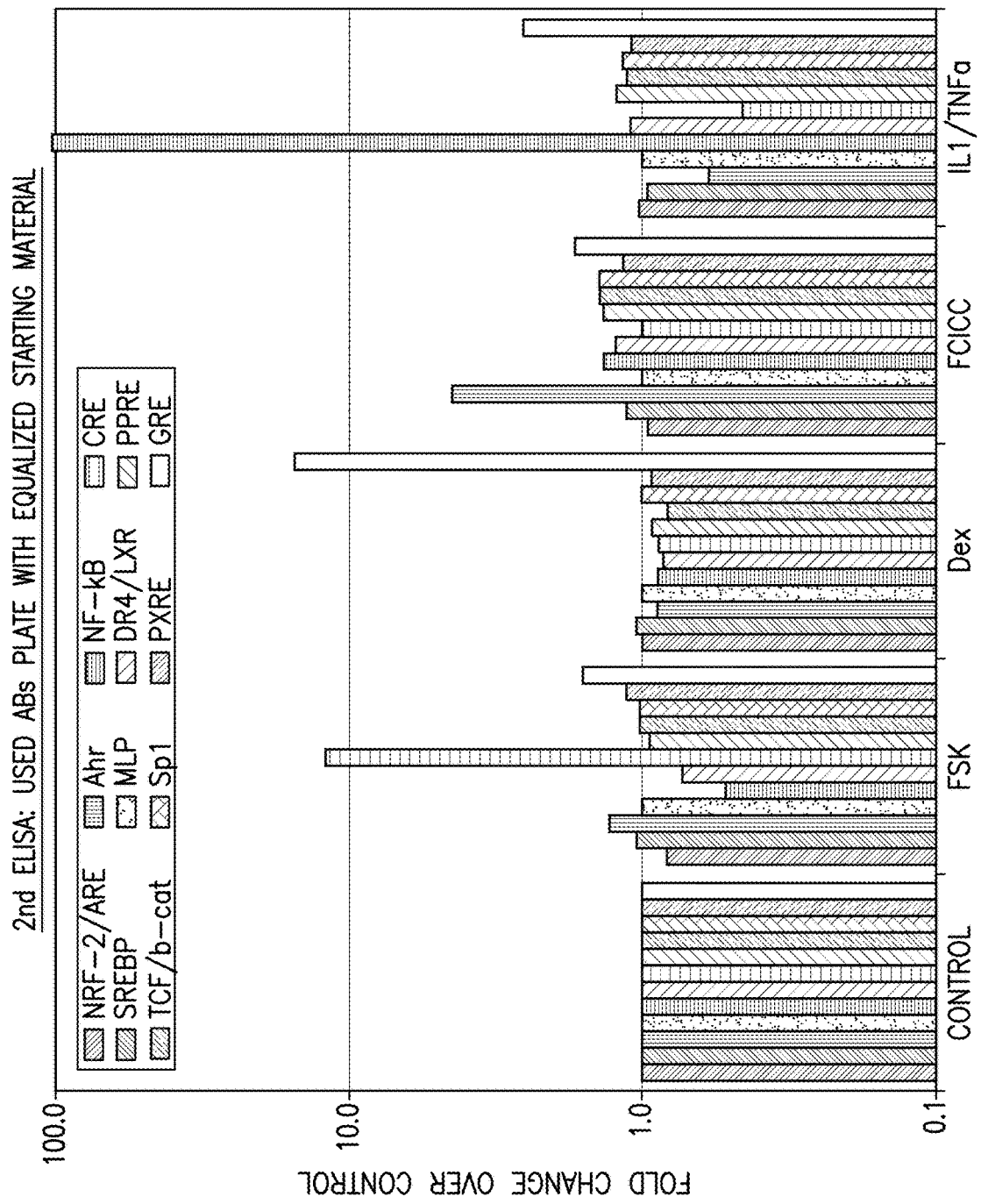
Figure 8C:
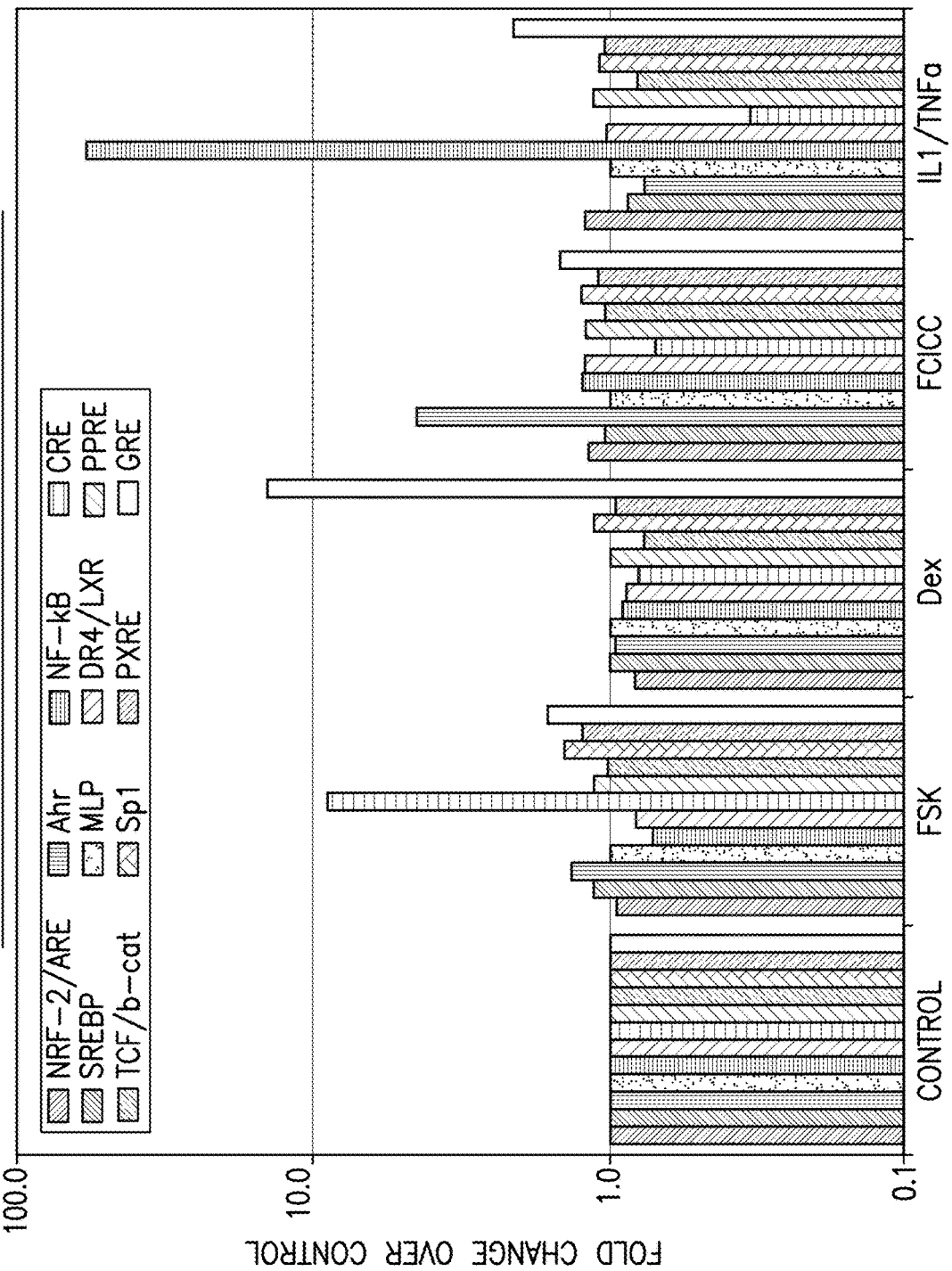
Figure 8D:
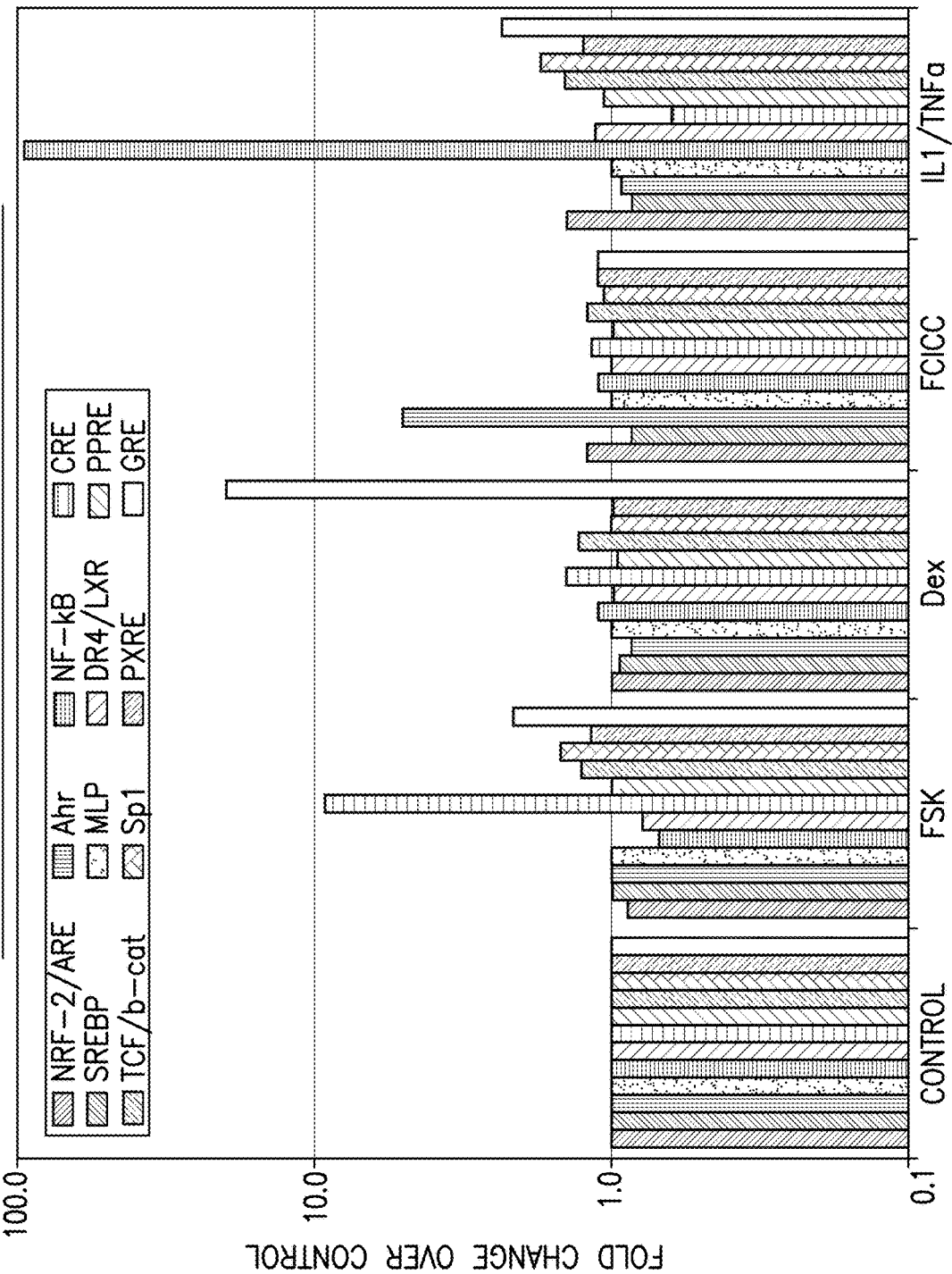

The multiplexing demonstration was further expanded to include twelve response elements/Gluc tags and twelve corresponding tag pulling antibodies to fit a 96-well format. FIG. 8 shows the result of four different assays that were conducted with different amounts of input signals on different antibody plates. Regardless the amount of input signal (FIGS. 8A and 8B: every well started with similar total RLU from different induction experiments; FIGS. 8C and 8D started with different total RLU but with the same dilution from original induction experiments) and amount of antibodies blotted on the wells (FIGS. 8A and 8D using same batch of antibodies plates, FIG. 8B having less antibodies and FIG. 8C having least antibodies in the well), all assays generated similar final results and all showed the specific induction from their corresponding inducers for FSK (CRE), Dexamethasone (GRE), FCICC (AhR) and IL-1β and TNF-α (NF-κB), respectively.

Figure 9A:
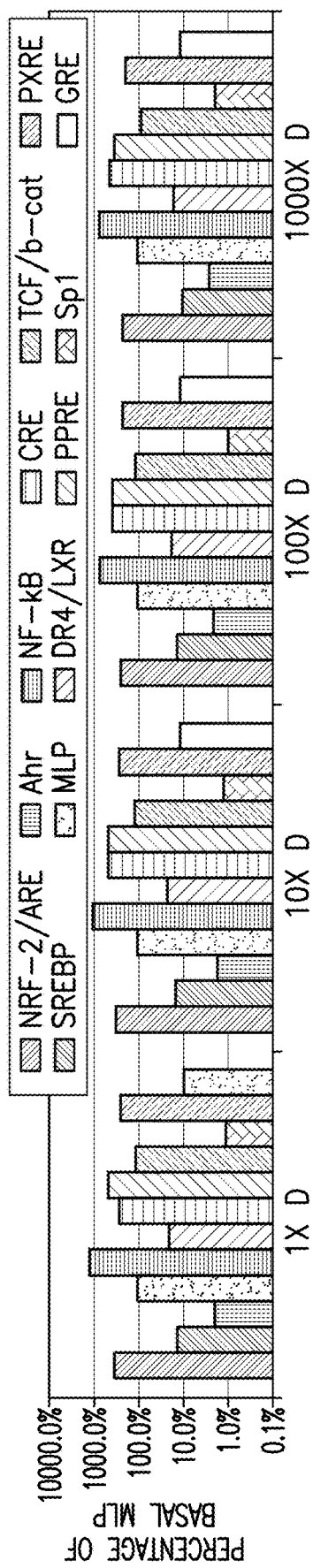
FIGS. 9A-C are graphs demonstrating the stability of the Gluc-tags profile with over 1000× dilution.
Figure 9B:
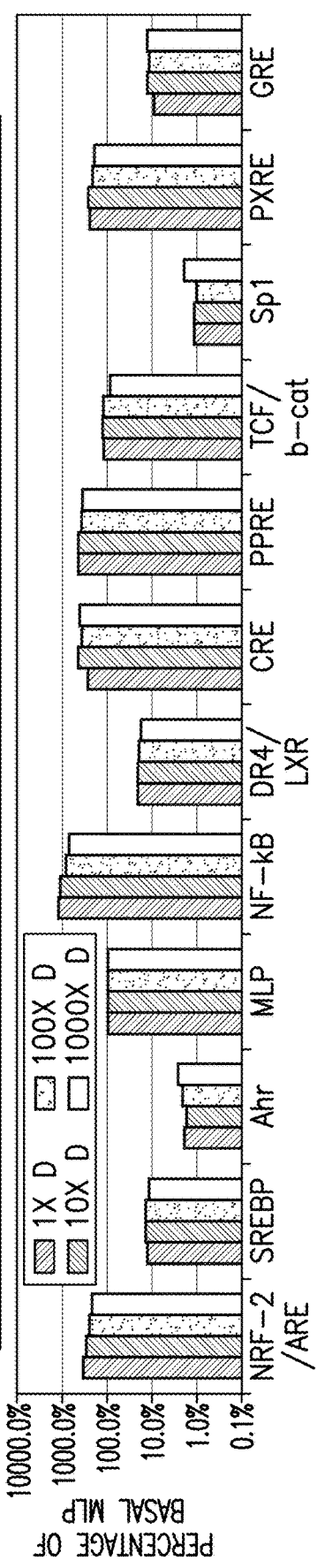
Figure 9C:
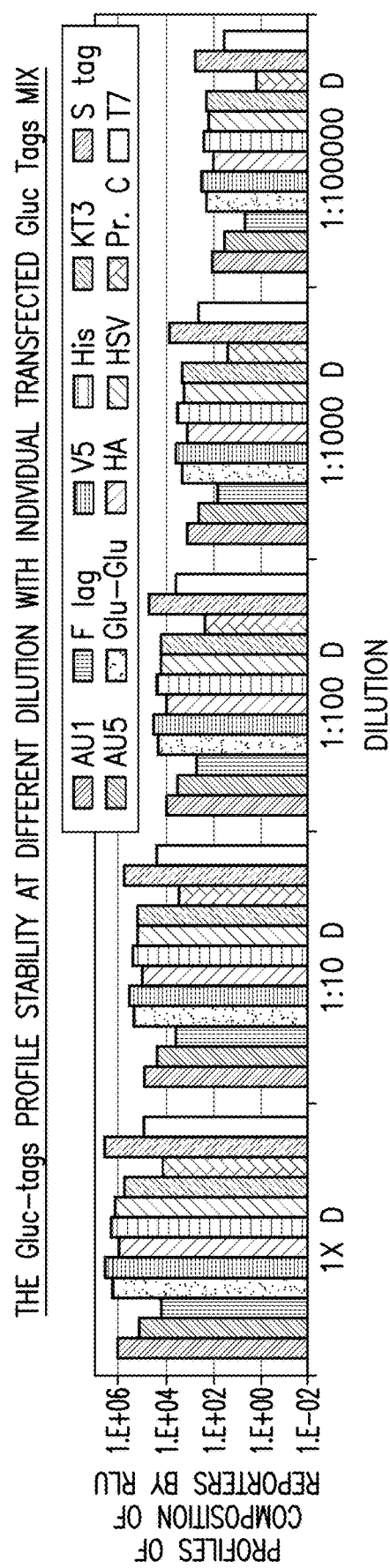

To construct a highly reliable multiplexing system with good reproducibility, the results must be stable and independent of the specific technique of detection. As indicated hereinabove, the multiplexing assay of the present disclosure has a strong degree of flexibility and high tolerance to the way in which the detection is conducted. The assay can start with equalized total RLU input for the detection; it also can start from original supernatant with different total RLU input; it can even start from any dilution which falls within the detection dynamic range, and still get the same results. FIGS. 9A-C demonstrate the profile stability with over 1000 times dilution. FIG. 9A and 9B started with the supernatant obtained from a multiplexing experiment in which premixed plasmids of different tagged reporters were transfected in 293H cells. The profiles of different dilutions were striking similar from 1× dilution to 1000× dilution. FIG. 9C shows the profiles from individual transfected tagged reporters, in which supernatants containing different tags were mixed together at a specific ratio after the transfection, with the readout of raw RLU being shown.

Figure 10:
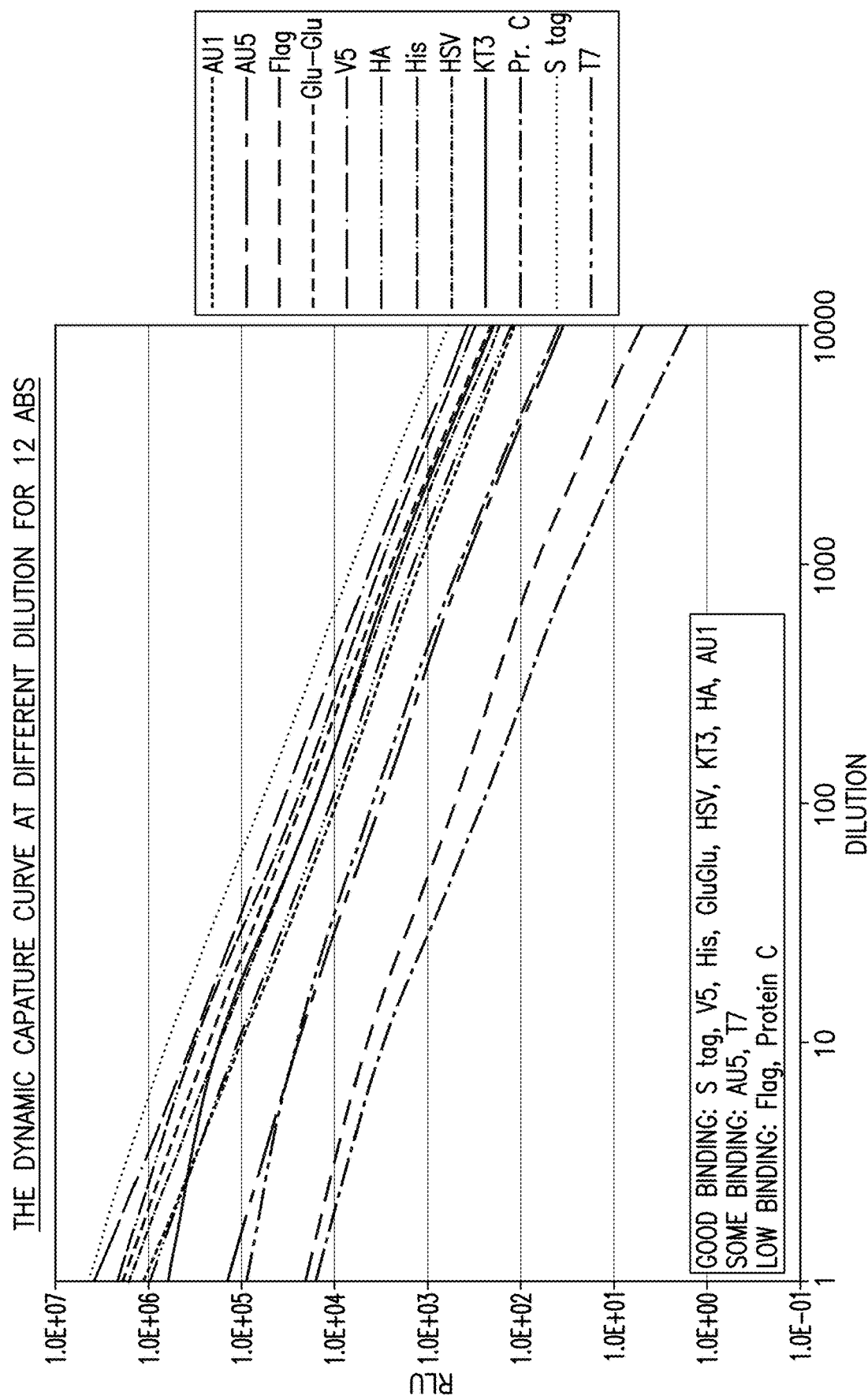
FIG. 10 is a graph illustrating the binding capacity curve for 12 antibodies: AI1, AU5, FLAG™ octapeptide marker tag DYKDDDDK (SEQ ID NO: 2), Glu-Glu, V5, HA, His, HSV, KT3, Pr. C, S tag, and T7.

It can be difficult to find antibodies against different tags, all with similar binding capacities, affinities and dynamic ranges. Accordingly, the assay system of the present disclosure provides a substantial advance in the art, since it does not require such absolute antibody similarities. FIG. 10 shows the binding capacity curve for 12 antibodies. These antibodies can be classified in three groups: a first group has strong binding and high capacity; a second group has intermediate binding behavior; and a third group has very low binding and capacity. All antibody groups have 1000 or more dynamic binding ranges, and regardless of how large the differences are among these antibodies, the final result is very stable as long as the same antibodies are used for each set of reporters in the assay. Corresponding considerations apply to aptamers when used as binding agents.

The above-discussed data demonstrate that the assay system has very high tolerance to different factors. The stability of the multiplexing reporter system of the present disclosure arises from its design. A basic backbone reporter is included in the mixture, which is common to all of the response element reporters, thereby serving to normalize the output so that the net effect derives from each individual response element. Since each single well has this internal control in the mixture, the variations among the wells, such as the differences of transfection efficiency and medium volume in the wells, the differences among different plates, the differences of dilution factor, will be normalized away and will not affect the final result. The characteristic uniformity of these reporters is essential to maintaining a similar environment among different wells after desired treatment and thereby avoiding unexpected effects. Regardless of the differences in individual antibodies and their binding capacities, each tagged reporter is compared against the same antibody independently of the other pulling antibodies, and this ensures that the final result is obtained from a true line by line comparison in the assay.

To further improve the reliability of this system, in one embodiment the disclosure provides an assay with two sets of tags for each response element. This provides uniformity and more definitive biological conclusions if both sets of reporters generate the same results. Such approach therefore is useful in avoiding any false results deriving from unforeseen interference effects on specific tags.

As previously mentioned, when protein is over-expressed in a cell, a substantial portion of the cell's resources are allocated to fulfill this demand. Over-expression of several different reporters or even a single strong endogenous reporter may result in severely adverse effects on the cell's growth and metabolic homeostasis. This stress can create unexpected side effects that interfere with the assay.

Figure 11A:
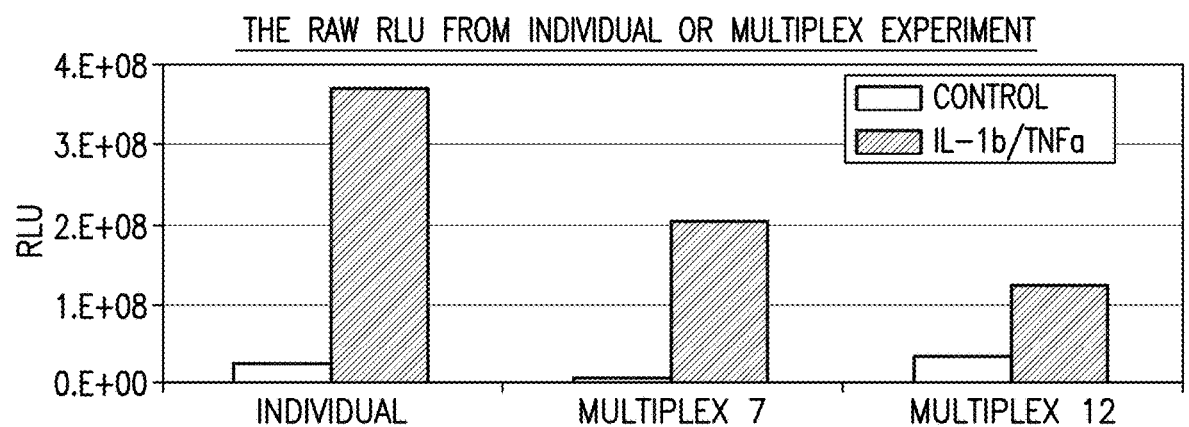
FIGS. 11A and B are graphs showing the raw RLU (11A) and the fold induction (11B) of individual and multiplex Glu-tag reporter assays.
Figure 11B:
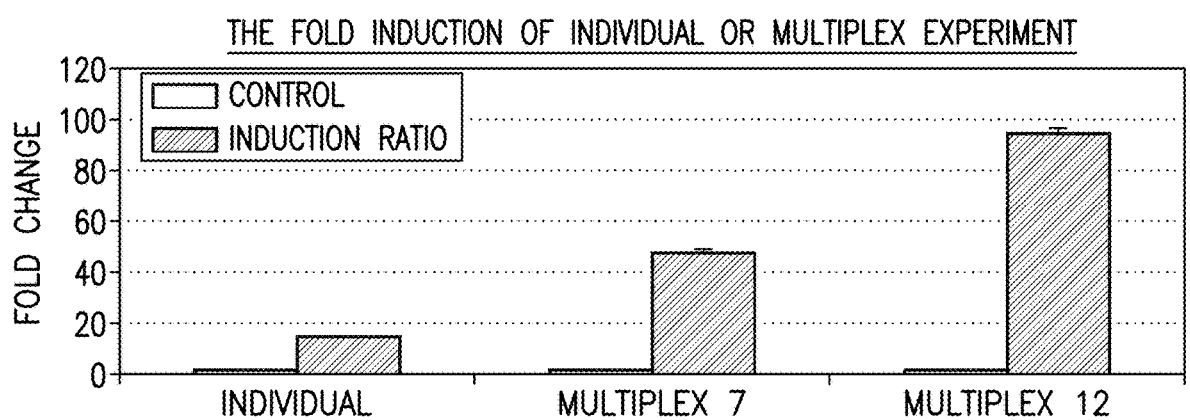
Figure 12B:
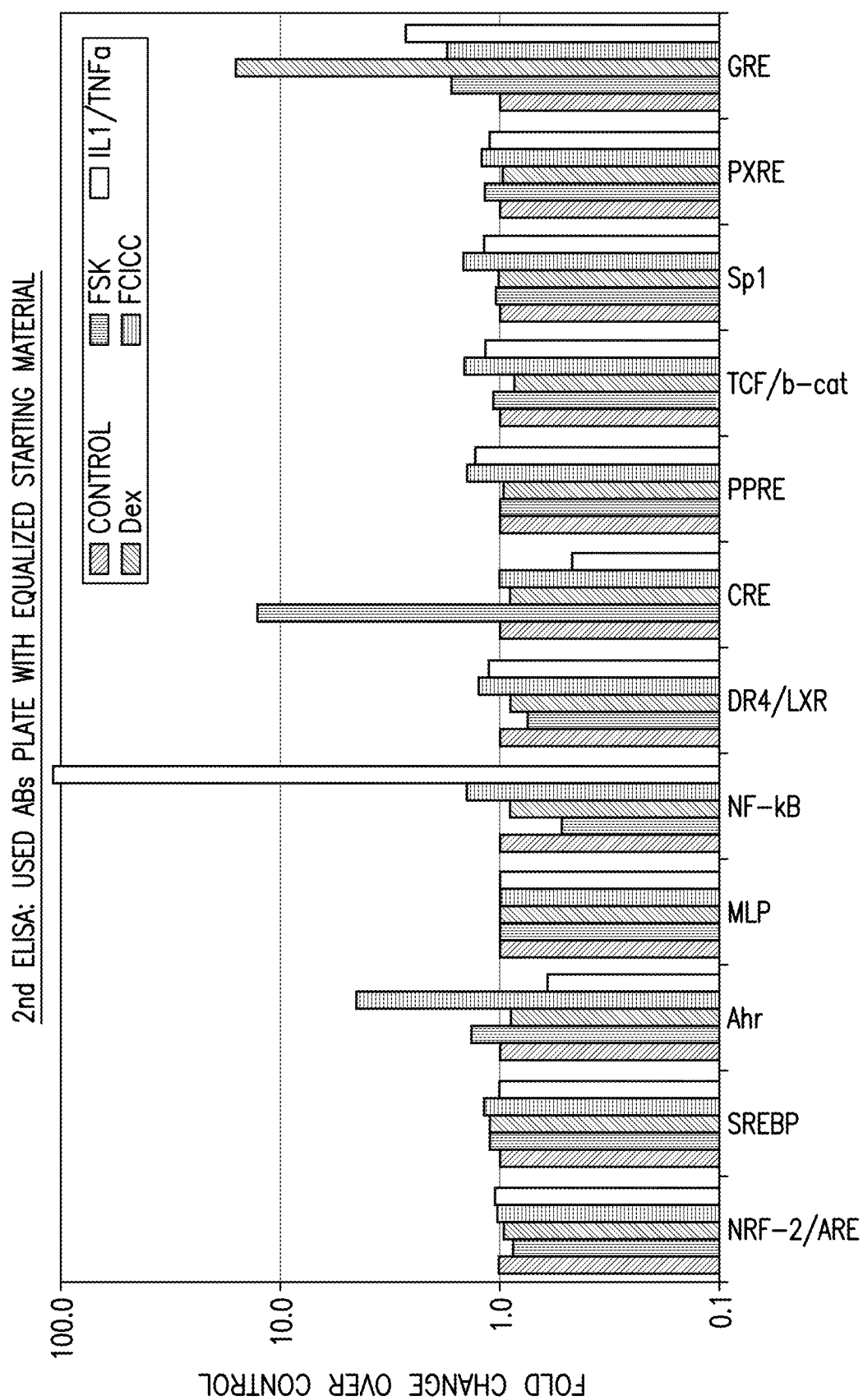

We have observed that the induction fold of some strong inducers increases with the degree of multiplexing. As shown in FIGS. 11A-B, the raw total RLU is highest in individual transfected cells (and could be higher if the cells' expression resources are not exhausted) and 12 multiplexed is the lowest. Multiplexing will downwardly adjust the signal from strong response elements to balance the weak ones to produce more even starting points. When induced, only one or a few response elements will respond and the others will remain the same, so the total RLU does not change as much as the individual RLU. But the induction fold change (FIGS. 12A-D) showed a different result, in which multiplexing gave much better fold induction and individual transfected cells showed the least. After multiplexing, achieving the full potential of induction requires much less of cells' resources (especially the corresponding TFs), so the true potential of induction is identified by multiplexing detection and underestimated by individual transfection. This can only be accomplished if the dynamic range of assay is broad enough to offset the total signal reduction and the dynamic range from the assay, e.g., the 8 magnitudes of dynamic range from Gluc assay, is sufficient to satisfy this requirement. To achieve efficient transfection, a certain amount of DNA is required. In this regard, to avoid exceeding the cells' expression capacity, the strong and highly inducible vector reporters should be diluted with mock DNA to obtain a reliable result in the individual reporter system.

The features of low background and high tolerance to the non-specificity of this new assay system enable true multiplexing screening.

The simple tagged reporter system of the present disclosure has many advantages over conventional reporter systems, as detailed below.

Only a "pulling antibody," the antibody specific to the tag of the recognition region is required for detection of the reporter. It can be easily applied to the bottom of the assay plate to get an equal and even amount in each starting well of a detection plate. When aptamers are employed as binding agents, corresponding advantages are realized.

By utilizing the same backbone in all reporters of a set or of a library, all reporters of that set or library have similar characteristics and therefore provide a uniform and comparable system to reproducibly reflect the activities of response elements placed in front of them in the reporter construct.

The tag, as a small fingerprint sequence attached to the C-terminus of each reporter in a set, gives each reporter of the set its own unique identity while still maintaining the uniformity of the whole system. By this design, the availability of peptide sequences for binding agents to cross-react is dramatically limited to the tagging region only and will reduce the possibility of nonspecific reactivity of the binding agents.

Cell culture supernatant can be taken directly from culture and applied directly to the wells of the detection plate and the specific targets (the reporters) can be pulled down by binding agent binding to the recognition region quantitatively without further manipulation of cells. After a simple washing step, the quantitation (e.g. numerical readout) is available. Unlike other image-based detection methods, no data conversion is needed, thereby reducing possible variations in the results. By avoiding the step of cell lysis, additional variations are reduced, along with possible binding problems due to use of dense lysate solution. The multiplexing assay and methods of the present disclosure result in more reliable and reproducible data for the response elements linked to each reporter.

The ultrawide dynamic range of the multiplexing assay of the present disclosure provides a very sensitive and quantitative assay to detect all reporters with various concentrations from trace amounts to highly abundant amounts.

The targets pulled down by binding agent detection are measured directly in the well. No detecting and/or secondary antibodies or aptamers are needed, and no secondary or tertiary labeling systems are required. This can avoid the specificity, sensitivity and background problems associated with such secondary or tertiary systems.

Since the quantification is from the pulled down reporter(s) only, the system has extremely high tolerance to non-specificity by design. The only requirement for the reactive antibodies or aptamers is lack of cross-reactivity with the core protein (i.e., Gluc backbone) and the short tag sequences. All other cross-relativities lack relevance to the final quantification and will not alter the final readout.

With the intrinsic reporter control in the multiplexing system, the amount of starting material and the difference of transfection efficiency among wells will not be an issue, and the supernatant can be diluted at any concentration as long as it is within the detection range. It will inherently offset the drug/inducers effect on basal promoters and therefore more accurately predict the effectiveness of the drug/inducers.

The high degree of multiplexing achievable by the assay of the present disclosure can markedly improve the detection sensitivity by avoiding cell resource system exhaustion due to over-expression. It will also substantially reduce the system stress for the cells employed for the assay, since only small fraction of system resources is needed for expression of each individual reporter. More accurate data can therefore be obtained on the full potential of an inducer.

In the assay method of the present disclosure, each binding agent functions independently of any other binding agents to pull one specific tagged reporter. Uniformity in binding affinity/capacity among antibodies or aptamers is not required, since cross comparison of antibodies or aptamers is not necessary. Therefore, the binding characteristics of antibodies or aptamers do not need to be same. Antibodies or aptamers with binding efficiency of over 1000× difference can be utilized in assay methods of the present disclosure.

The 96-well format ELISA described herein is provided as an example of the utilization of a system of the present disclosure. It is contemplated herein that the systems of the present disclosure may be applied, expanded or increased to any known throughput system, such as those with 192, 384, 1632, or other number of well plates, as long as a luminometer is available for the plate format.

In a still further embodiment, the systems of the present disclosure may include reuse of binding agent plates, after proper treatment to prepare the plates for reuse.

Similar results have been obtained using protein A/G agarose beads (combined with filter plates for washing) through immuno-precipitation (IP). Purified antibodies are not required in this case and therefore it is a good alternative when only low amount of ascites fluid, serum or culture media are available as the antibody sources. Since antibody/antigen interaction is conducted three-dimensionally rather than two-dimensionally as in ELISA, the binding efficiency is higher, but the procedure is more complicated and therefore variation will be larger.

Glass slide microarrays can also be used for analysis in accordance with the present disclosure, and satisfactory images have been obtained from these experiments by CCD camera.

Fluorescent scanners have been widely used for DNA chip and protein arrays with strong signals. Although modification of systems of the present disclosure by using fluorescent labeling to get a final readout is contemplated, such use does not permit direct enzyme labeling as described herein, unless ultrahigh sensitivity luminescent scanners are employed. A micro-column with different antibodies sections, either in disposable or reusable forms, is also contemplated for detection use in the present system. A microfluidics chip-based device can also be utilized for the detection. Multiple antibodies or aptamers can spotted on the fluid path to immobilize the specific target and multiple samples can be applied at same time to achieve high throughput. Membrane-based assays can also developed using the multiplexing approach of the present disclosure.

Luminex microsphere technology (Luminex, Austin, Tex.) can be used to provide multiplexing capacity, which in theory can provide 100 multiplexing using color coded beads. The full capacity of such microsphere technology for analyzing native proteins is not susceptible of achievement because of certain limitations: 1) the density of protein solution requirement poses difficulties, since excessively high density (such as in cell lysate) will interfere with the interaction with the beads, and excessively low density result in underdetection, so the application of such microsphere technology is more suitable for blood chemistry analysis; 2) the affinity of antibodies requirement poses difficulties, since strong binding to the target is required, without cross-reaction with the remainder of the proteins, and the more proteins on the list, the higher the possibility of cross-reactivity; and 3) the concentration of different targeted proteins should be more or less even to avoid under-estimation or under-detection, since the detection dynamic range is not high with single bead fluorescent measurement. As a result of the foregoing issues, multiple native proteins have to be regrouped into much smaller subgroups based on their characteristics and cross-reactivity to achieve optimal results. In a further embodiment of the present disclosure, an induced library of tagged reporters is analyzed by Luminex beads technology, wherein the fluorescent detector is replaced with a luminescent detector. The drawbacks of using individual targeted protein antibodies or aptamers will not be an issue for this multiplexing system, and therefore the throughput can be dramatically improved with such colored coded beads.

The TF response elements are illustratively described herein for purposes of demonstration. Any multiple gene activity analyses can be carried out with multiplexing systems of the present disclosure. Whole genome analysis can also be conducted by either randomly or specially targeted integration.

Accordingly, systems of the present disclosure are further contemplated in screening potential drug targets. Use of systems of the present disclosure enables rapid identification from the individual responsive tagged reporters, of any change from control conditions, thereby permitting identification of candidate drug targeted genes and evaluation of toxic effects on known genes or transcription factors.

The tagged reporter systems of the present disclosure can in theory provide unlimited numbers of reporters with similar characteristics. By using enzyme reporters directly and applying the simple one-step detection method from a supernatant, reproducible numeric data can be obtained with a broad dynamic detection range, high degrees of flexibility in sample composition and dilution, high tolerance to variations from transfection efficiency and well-to-well differences, and lower stringency requirements for the antibodies' specificity and binding efficiency. Multiplexing can be achieved either by co-transfection or individual transfection followed by mixing to realize desired target groups, and every multiplexed component in the set will be under the exact same conditions within the same well of the assay plate.

It will be recognized that the recognition region of protein reporters utilized in the practice of the present disclosure may be widely varied to facilitate binding and detection, and may comprise any suitable recognition site that is fused in frame to the reporter sequence, for binding by aptamers, antibodies, or other binding agents or media. The recognition region therefore may comprise an epitope appropriate for such binding.

The multiplexed detection of reporter constructs can be carried out with the sample containing one or more transcription factors being constituted by an organ of an animal, with a transfection system of the present disclosure being introduced to the organ of the animal, e.g. to a liver of a mouse or rat, with multiplexing detection being carried out on blood taken from the animal. The detection may involve secreted proteins such as luciferase or other bioluminescent enzymes, with detection of such bioluminescent enzyme in vivo after transfection. For example, luciferase may be utilized as the secreted protein, with circulating luciferase serving as a marker for transfection efficiency. Stability of the reporter protein can be increased using proteins such as albumin.

Figure 15:
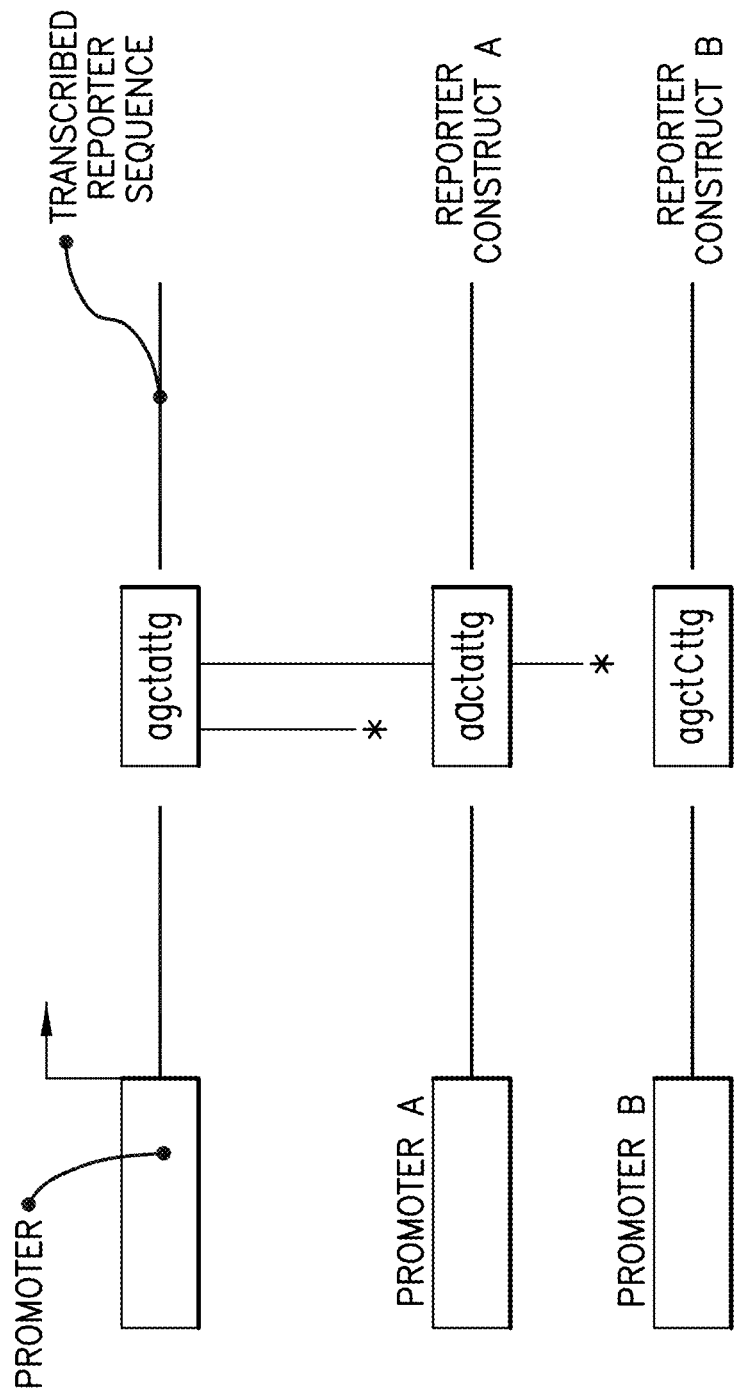
FIG. 15 shows reporter constructs of a library including reporter construct A and reporter construct B, according to one embodiment of the disclosure.

The disclosure contemplates a wide variety of constructs and methods for multiplexed detection of reporter constructs. In one aspect, a library of reporter constructs is contemplated, in which each construct contains a promoter functionally linked to a reporter system so as to control transcription of the reporter sequence. Each reporter in the library is identical, but contains a sequencing tag allowing for unequivocal distinguishing of the reporter sequences within the library by sequencing, wherein the sequencing tag comprises a substitution of one or several nucleotides in a tag sequence of the reporter. FIG. 15 shows reporter constructs of a library including reporter construct A and reporter construct B.

The process of multiplexed detection of promoter activities of such constructs comprises introducing the library of reporter constructs into a cell system to be evaluated. The introduction may be affected by any suitable technique, e.g., by transient transfection, stable transfection, or any other transfection technique enabling transcription of reporter sequences within cells, such as lipofection, electroporation, biolistic delivery, etc. Cell systems to be evaluated in such process may comprise a cell culture, and organ culture, a whole organ of an animal, a tissue of an animal, or any other suitable cell system. The transcribed reporter RNA expressed by the reporter constructs is reverse transcribed to yield reporter cDNAs, which then are amplified, e.g., by PCR, linear amplification, rolling circle amplification, or other sequence-specific amplification using a common pair of primers complementary to the reporter sequence outside of the sequencing tag. The amplified cDNAs are then sequenced. The activity of a given reporter construct then can be determined by determining the number of cDNAs transcribed by a given reporter construct, by assessing numbers of reporter cDNAs containing the sequencing tag at a defined position. Next, activities of reporter constructs within the evaluated cell system are determined by calculation of the ratio of reporter cDNAs transcribed by each reporter construct.

In such process, the sequencing of the amplified cDNAs may be carried out after separating them from irrelevant DNAs, e.g., by providing an isolation tag within the PCR primers and using corresponding separation reactions. For example, nucleotides of PCR primers may contain a biotin tag so that the amplified PCR products can be separated using a streptavidin-conjugated column, or the PCR primers may contain nucleotides labeled with ferromagnetic beads and separated by magnetic field, or a peptide epitope that can be separated using immobilized antibodies, or any other suitable separation technique.

Figure 16:
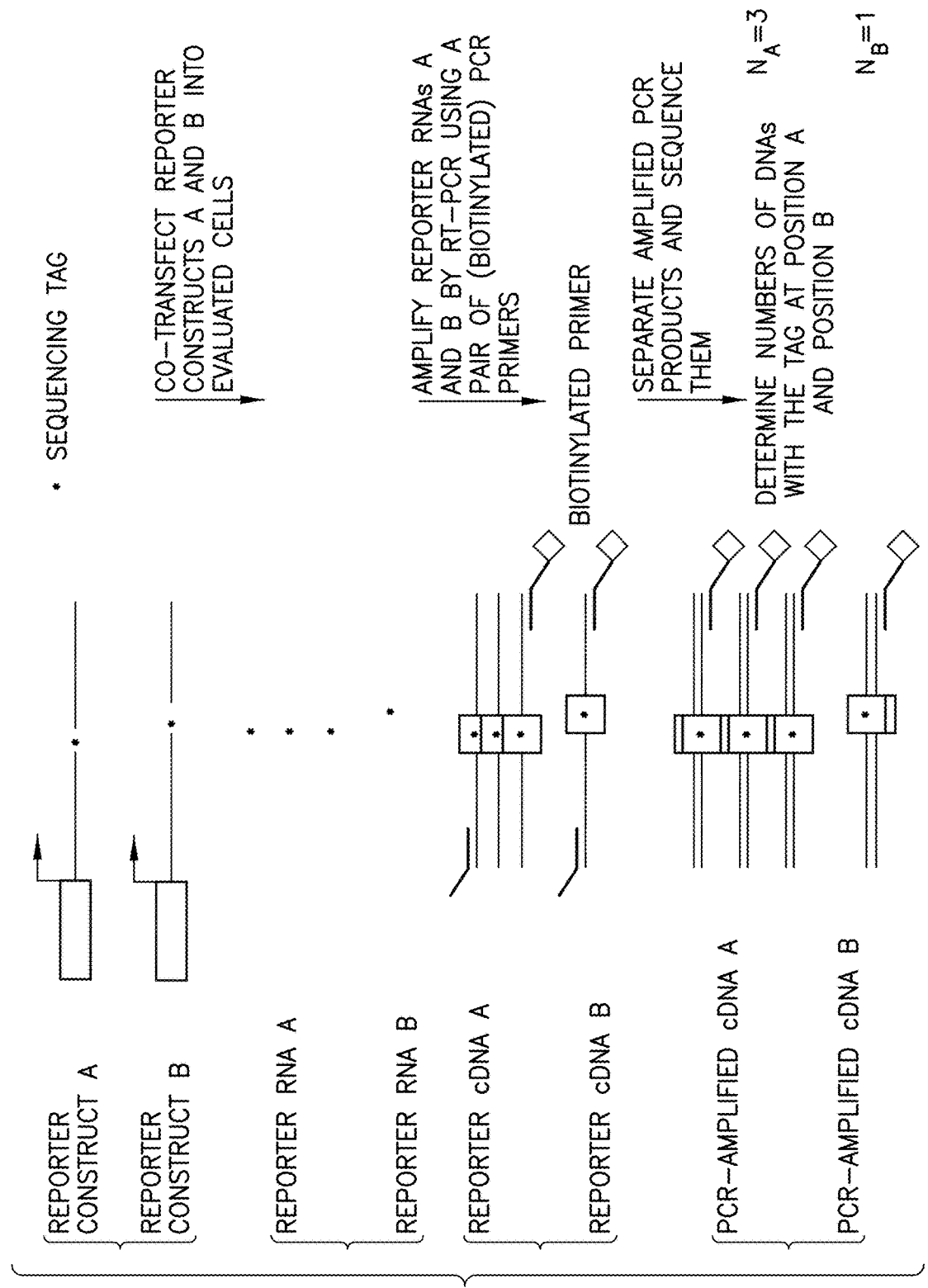
FIG. 16 shows schematically a process of multiplexed detection of promoter activities.

FIG. 16 shows schematically a process of multiplexed detection of promoter activities.

The disclosure additionally contemplates a process for multiplexed detection of reporter constructs in multiple cell systems, comprising transfecting a reporter construct library into one or more evaluated cell systems (e.g., 1, 2, 10, 100, 1000, or more in number). Reporter cDNAs in each evaluated cell system are amplified using a pair of PCR primers, common for each cell system, complementary to the reporter sequence outside of the sequencing tag and identifier sequence tag outside of the primer sequence complementary to the reporter sequence. All reporter constructs are sequenced. Activities of a given reporter construct in a given evaluated cell system are determined by determining the number of cDNAs containing the identifier sequence tag and the sequencing tag at a defined position. The profile of reporter construct activities in the evaluated cell systems then is determined by calculating cDNAs transcribed by each reporter construct within evaluated cell systems by counting reporter cDNAs containing the sequencing tags at defined positions and the identifier tags.

Figure 17:
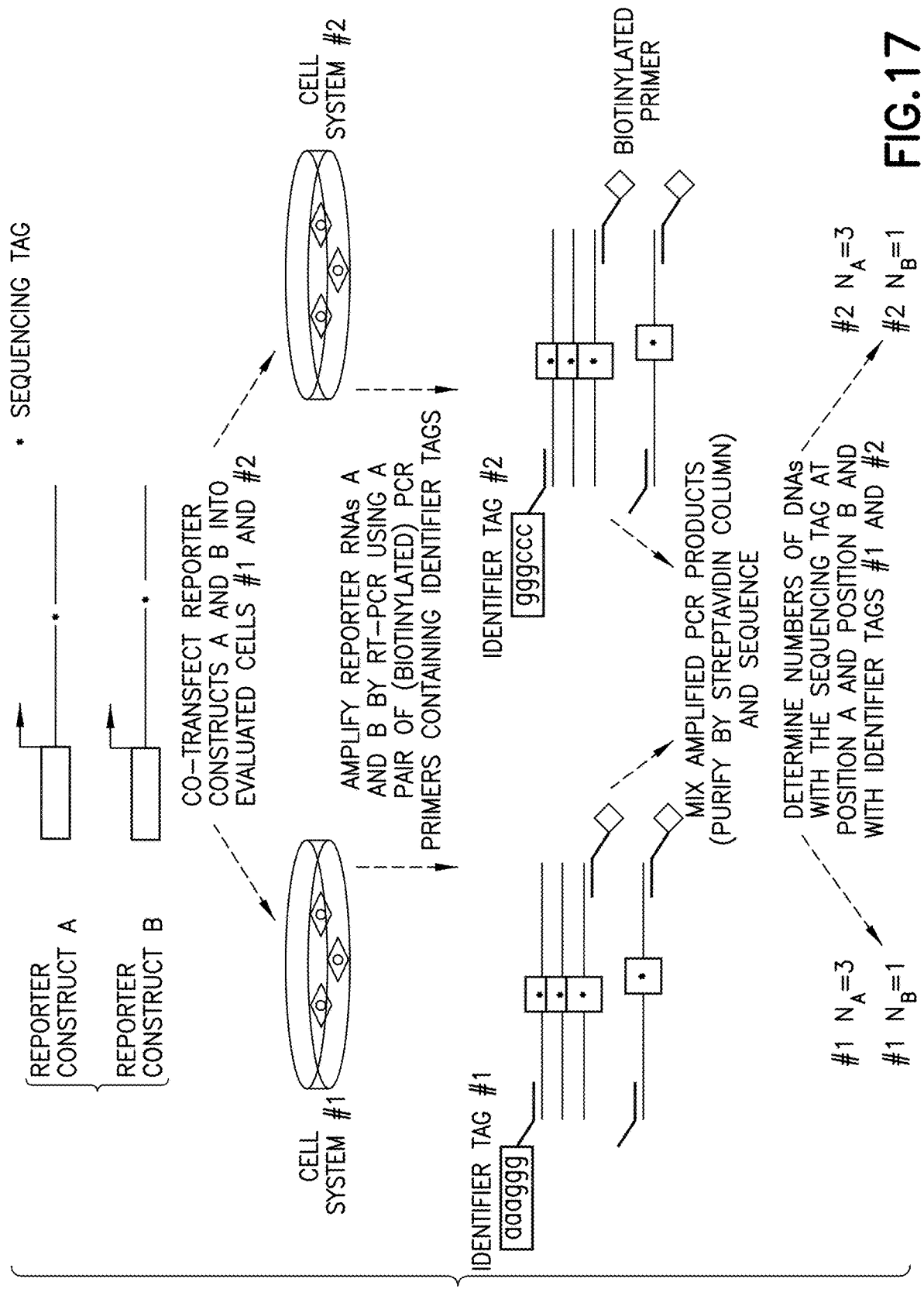
FIG. 17 schematically shows a process for multiplexed detection of reporter constructs in multiple cell systems.

FIG. 17 schematically shows a process for multiplexed detection of reporter constructs in multiple cell systems.

Systems of the present disclosure may be combined with current advanced screening methods to enable fully automatically handling by common liquid handlers. Such combination provides a powerful high-degree multiplexing system, not only in TF reporter system analysis, but also for any gene/gene groups' profiling, whole genome analyzing, drug screening and drug toxicity studies.

The advantages and features of the invention are further illustrated with reference to the following examples, which are not to be construed as in any way limiting the scope of the invention but rather as illustrative of embodiments of the invention in specific applications thereof.

EXAMPLE 1

Construction of Reporter Plasmid Constructs

A linker with XbaI and Fse I digestion sites was inserted after the last amino acid codon of Gluc peptide. Different 5-15 amino acid length tags were inserted between XbaI and Fse I, using adaptors. Standard molecular cloning techniques were used.

Where Gluc was used as the reporter, constructs for all of Gluc-6×His, Gluc-c-Myc, Gluc-V5, Gluc-FLAG™ octapeptide marker tag DYKDDDDK (SEQ ID NO: 2), Gluc-HA, Gluc-Glu-Glu, Gluc-VSV-G, Gluc-T7, Gluc-S tag, Gluc-protein C, Gluc MAT™ heptapeptide marker tag HNHRHKH (SEQ ID NO: 3), Gluc-KT3, Gluc-IRS, Gluc-HTTPHH (SEQ ID NO: 1), Gluc-HSV, Gluc-B tag, Gluc-AU5, and Gluc-AU1 were generated under a CMV promoter and the protein was expressed in 293H and HepG2 cells.

Where SEAP was used as the reporter, constructs for all of SEAP-6×His, SEAP-c-Myc, SEAP-V5, SEAP-FLAG™ octapeptide marker tag DYKDDDDK (SEQ ID NO: 2), SEAP-HA, SEAP-Glu-Glu, SEAP-VSV-G, SEAP-T7, SEAP-S tag, SEAP-protein C, SEAP-MAT™ heptapeptide marker tag HNHRHKH (SEQ ID NO: 3), SEAP-KT3, SEAP-IRS, SEAP-HTTPHH (SEQ ID NO: 1), SEAP-HSV, SEAP-B tag, SEAP-AU5, and SEAP-AU1 were generated under a SV40 promoter and the protein was expressed in 293H and HepG2 cells.

EXAMPLE 2

High Throughput Reporter Assay

Purified Antibodies were diluted in DPBS with 5% glycerol at 5 µg/ml concentration. 50 µk of diluted antibody solutions were dispensed onto wells of a LUMITRAC 600 plate (Greiner Bio-One, Monroe, N.C.), and the plate was tapped gently to distribute the antibody solutions evenly on the bottom of the well. The plate was sealed tightly with a PCR sealing film. The antibody plate was stored at 4° C. for one week for antibodies to bind.

At the end of incubation, 200 µl of Blocking Reagent (Attagene, Research Triangle Park, N.C.) was added to the wells to block the unbounded surface, either for 1 hour at room temperature for quick use, or at 4° C. overnight. The plate was washed 4 times with DPBS (Invitrogen, Carlsbad, Calif.) by flicking the solution out into a waste container and then blotted dry briefly on layers of paper towel. Target samples were diluted in Binding Reagent (Attagene, Inc., Research Triangle Park, N.C.). After the washing, 100 µl of diluted testing samples were added to the well and incubated at RT for 1 hour with gentle rocking agitation.

After the incubation, samples were removed by gently flicking and the plate was washed 4 times with DPBS as above. After the last wash, 30 µl of DPBS were dispensed into the well to cover the whole bottom of the well and the Gluc activity was measured by injecting 40 µl of substrate with an integration time of 5 seconds. The reading was normalized against the minimal promoter driven reporter.

EXAMPLE 3

Tissue Culture

HepG2 and 293H cells were grown in high glucose DMEM medium (Invitrogen, Carlsbad, Calif.) with 10% FBS (Hyclone, Logan, Utah) and 1× antibiotics solution (Invitrogen, Carlsbad, Calif.) at 37° C. and 5% $CO_2$.

Figure 13A:
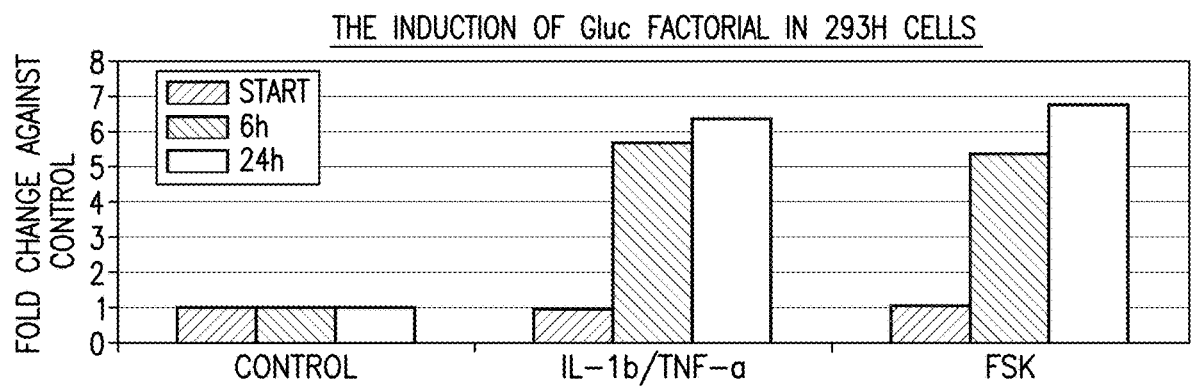
FIGS. 13A and 13B are graphs of the induction of the Gluc Factorial and Regular Factorial in 293H cells.
Figure 13B:
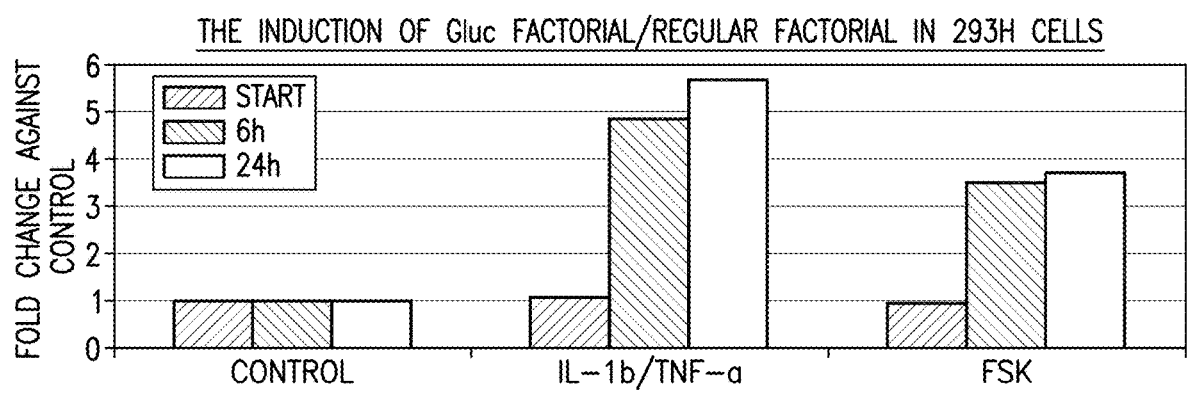

Gluc Factorial and Regular Factorial assays were carried out in the 293H cells (Regular Factorial assays being more fully described in U.S. Patent Application Publication 20100009348 of Sergei Romanov, et al., the disclosure of which is hereby incorporated herein by reference). The results are shown in FIGS. 13A and 13B.

Figure 14:
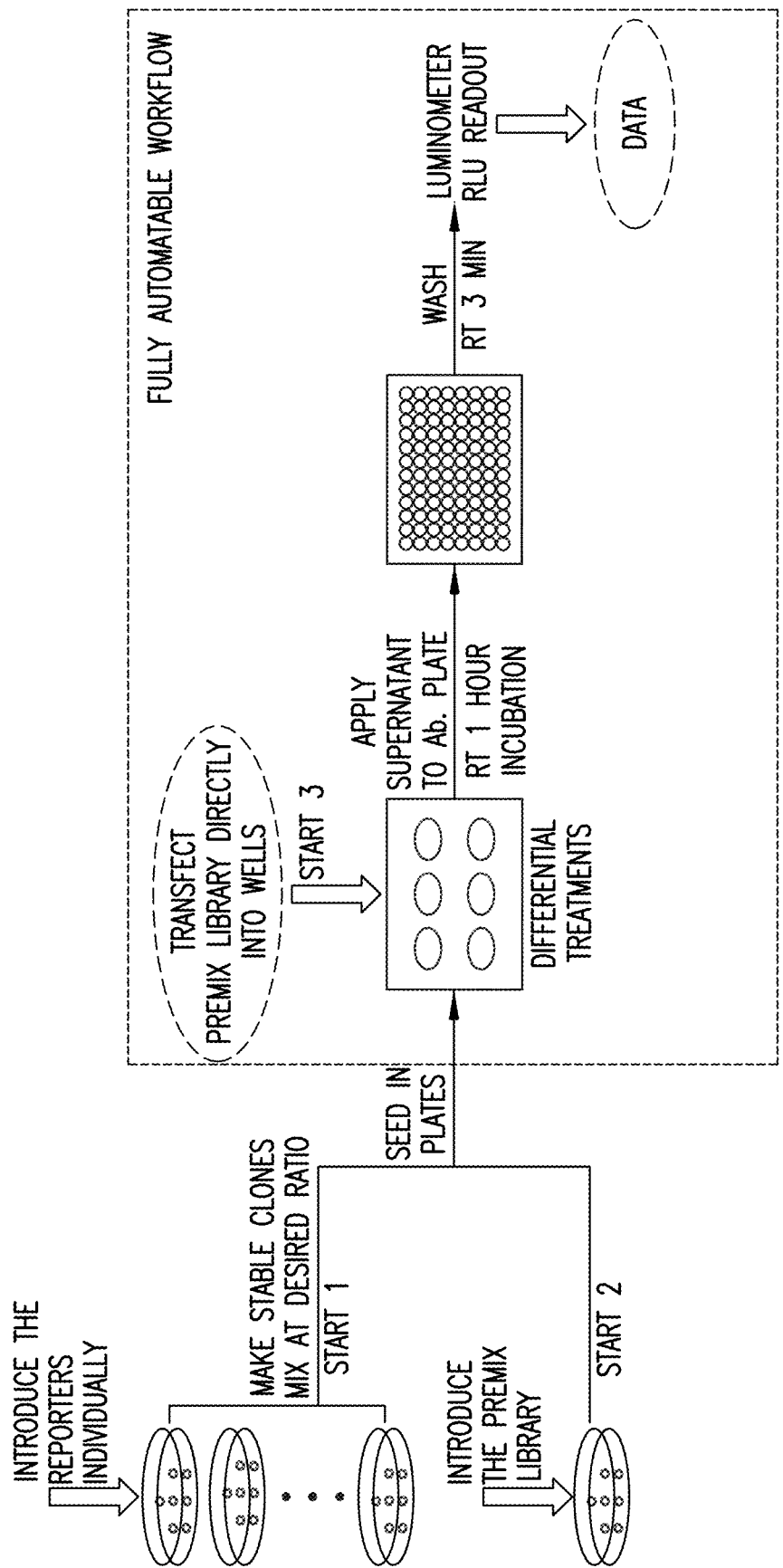
FIG. 14 is an illustration of an exemplary assay of the invention.

FIG. 14 is an illustration of an exemplary assay system and process according to one embodiment of the invention. Reporters are introduced individually and employed to make stable clones that are mixed at a desired ratio, or alternatively a premixed library of reporters is utilized. The reporter material then is seeded in plates. Alternatively, a transfected premixed library may be introduced directly into wells. Following 1 hour incubation at room temperature, supernatant is applied to an antibody plate. Washing is conducted at room temperature for 3 minutes, followed by luminometer RLU readout to quantitate the activities of multiple transcription factors. The sequence shown in FIG. 14 can be implemented in a fully automated workflow system and process, for high throughput assay operation.

While the disclosure has been has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A gene construct library for expression of a protein reporter system in cells of a sample for simultaneous quantitative assessment of activity of multiple transcription factors in said sample, when said cells are transfected with the gene construct library and said protein reporter system is expressed therein, said gene construct library comprising at least two gene construct sets, wherein each gene construct set comprises a multiplicity of gene constructs, wherein each of said gene constructs comprises:

- a response element responsive to binding of a transcription factor of said multiple transcription factors in said sample;
- a backbone comprising an open reading frame of a secreted enzyme; and
- a recognition region comprising a tag sequence of nucleotides, downstream of the backbone, wherein in each of the sets, the recognition region tag sequence of each gene construct in the set differs from the recognition region tag sequence of any other gene construct in the set, but wherein each gene construct in the set is otherwise identical to all other gene constructs in the set, wherein the secreted enzyme of the backbone open reading frame is the same in all gene constructs and all sets in the library, and wherein the gene construct sets in said library differ from each another by their respective response elements.

2. The gene construct library of claim 1, wherein the recognition region tag sequence of nucleotides encodes a tag amino acid sequence of from 5 to 15 amino acids.

3. The gene construct library of claim 1, wherein the backbone comprises an open reading frame of Gaussia luciferase (Gluc) or secreted embryonic alkaline phosphatase (SEAP).

4. The gene construct library of claim 1, wherein the recognition region tag sequence of each gene construct in each set encodes a different tag selected from the group consisting of 6×His, c-Myc, V5, octapeptide marker tag DYKDDDDK (SEQ ID NO: 2), HA, Glu-Glu, VSV-G, T7, S tag, protein C, heptapeptide marker tag HNHRHKH (SEQ ID NO: 3), KT3, IRS, HTTPHH (SEQ ID NO:1), HSV, B tag, AU1, and AU5.

5. A cellular sample comprising cells transfected with the gene construct library of claim 1, wherein said cells contain said multiple transcription factors to which response elements of gene constructs in said library are responsive, and wherein the secreted enzyme is exogenous to the cells of the sample.

6. The cellular sample of claim 5, wherein the sample is a cell culture, an organ culture, a whole organ of an animal, or a tissue of an animal.

7. A gene construct library for expression of a protein reporter system in cells of a sample for simultaneous quantitative assessment of activity of multiple transcription factors in said sample, when said cells are transfected with the gene construct library and said protein reporter system is expressed therein, said gene construct library comprising at least two gene construct sets, wherein each gene construct set comprises a multiplicity of gene constructs, wherein each of said gene constructs comprises:

- a response element responsive to binding of a transcription factor of said multiple transcription factors in said sample;
- a backbone comprising an open reading frame of a secreted enzyme; and
- a recognition region comprising a tag sequence of nucleotides, downstream of the backbone, wherein in each of the sets, the recognition region tag sequence of each gene construct in the set differs from the recognition region tag sequence of any other gene construct in the set, but wherein each gene construct in the set is otherwise identical to all other gene constructs in the set, and wherein the response element in each set is independently selected from the group consisting of peroxisome proliferator response elements (PPRE), pregnane X response element (PXRE), cAMP response element (CRE), Major late promoter (MLP), direct repeat 4 (DR4), glucocorticoid response element (GRE), Specificity Protein 1 response element (Sp1), and antioxidant response element (ARE).

* * * * *